US006500433B1

(12) United States Patent
Lehner et al.

(10) Patent No.: US 6,500,433 B1
(45) Date of Patent: *Dec. 31, 2002

(54) **POLYPEPTIDE FRAGMENTS CAPABLE OF COMPETITION WITH *STREPTOCOCCUS MUTANS* ANTIGEN I/II**

(75) Inventors: Thomas Lehner, London (GB); Charles Kelly, London (GB)

(73) Assignee: The Council of Governors of the United Medical & Dental School of Guy's and St. Thomas's Hospitals (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/456,474

(22) Filed: Dec. 9, 1999

Related U.S. Application Data

(62) Division of application No. 08/894,017, filed on Oct. 20, 1997, now Pat. No. 6,024,958.

(30) Foreign Application Priority Data

Jan. 31, 1995 (GB) ............................................... 9501826
Jan. 31, 1996 (WO) .............................. PCT/GB96/00207

(51) Int. Cl.[7] ........................ A61K 39/00; A61K 39/02; A61K 39/09; C07K 7/00

(52) U.S. Cl. ............................... 424/190.1; 424/185.1; 424/190.1; 424/244.1; 530/300; 530/324

(58) Field of Search ............................... 530/300, 324, 530/325, 326, 327, 328, 329; 424/190.1, 185.1, 244.1, 181.1

(56) References Cited

U.S. PATENT DOCUMENTS 5,258,368 A  11/1993  Lewicki et al. ............... 514/12

FOREIGN PATENT DOCUMENTS

| EP | 116472 | 2/1984 |
|---|---|---|
| EP | 280576 | 2/1988 |
| GB | 2060647 | 5/1981 |

OTHER PUBLICATIONS

Bell et al. 1992. Definition of an immunodominant T cell epitope in the envelope gp41 sequence of HIV–1. Clin. Exp. Immunol. vol. 87, pp. 37–45.*
Adorini et al., "Mechanisms Influencing the Immunodominance of T Cell Determinants," J EXP MED (1988) 168:2091–2104.
Barnett et al., "The Immune Response of BALB/C Mice of Influenza Hemagglutinin: Commonality of the B Cell and T Cell Repertoires and their Relevance to Antigenic Drift," EUR J IMMUNOL (1989) 19:515–521.
Brady et al., "Differentiation of Salivary Agglutinin–Mediated Adherence and Aggregation of Mutans Streptococci by Use of Monoclonal Antibodies Against the Major Surface Adhesion P1," Infection And Immunity (1992) 60(3):1008–1017.
Burgess et al., "Possible Dissociation of the Heparin–Binding and Mitogenic Activities of Heparin–Binding Activities by Site–Directed Mutagenesis of a Single Lysine Residue," J Cell Biol (1990) 111:2129–2138.
Charles et al., "Identification and Characterization of a Protective Immunodominant B Cell Epitope of Pertactin (P.69) from *Bordetella pertussis*," Eur J Immunol (1991) 21:1147–1153.
Emsly et al., "Structure of *Bordetella pertussis* Virulence Factor P.69 Pertactin," Nature (1986) 4381:90–92.
Greenstein et al., "A Universal T Cell Epitope–Containing Peptide from Hepatitis B Surface Antigen Can Enhance Antibody Specific for HIV gp120," J Immunol (1992) 148:3970–3977.
Jacobs et al., "Molecular Mimicry by *Mycoplasma pneumoniae* to Evade the Induction of Adherence Inhibiting Antibodies," J Med Microbiol (1995) 43:422–429.
Kelly et al., "Genetic and Immunological Analysis of Conserved Epitopes of Antigen I/II in Oral Streptococci," J Dent Res (IADR Abstracts, Abstract 17) (1992) 71:517.
Kelly et al., "T–Cell, Adhesion, and B–Cell Epitopes of the Cell Surface *Streptococcus mutans* Protein Antigen I/II," Infection and Immunity (1995) 63(9):3649–3658.
Kendal et al. (Abstract 234), Todryk et al. (Abstract 235), Ma et al. (Abstract 238), J Dent Res (1994) 73(4):816.
Lazar et al., "Transforming Growth Factor α: Mutation of Aspartic Acid 47 and Leucine 48 Results in Different Biological Activities," Mol Cell Biol (1988) 8(3):1247–1252.
Lehner et al., "T–Cell and B–Cell Epitope Mapping and Construction of Peptide Vaccines," Molecular Pathogenesis of Periodontal Disease (Genco et al. ed., American Society for Microbiology 1994) Chapter 24:279–292.
Moisset et al., "Conservation of Salivary Glycoprotein–Interacting and Human Immunoglobulin G–Cross–Reactive Domains of Antigen I/II in Oral Streptococci," Infection and Immunity (1994) 62(1):184–193.
Munro et al., "A Protein Fragment of Streptococcal Cell Surface Antigen I/II which Prevents Adhesion of *Streptococcus mutans*," Infection and Immunity (1993) 61(11):4590–4598.
Munro et al., "Mapping of Adhesion Epitopes of Streptococcal Antigen I/II," J Dent Res (IADR Abstracts, Abstract 1753) (1992) 71:735.
Neurath et al., "Identification and Chemical Synthesis of a Host Cell Receptor Binding Site on Heptitis B Virus," Cell (1986) 46:429–436.

(List continued on next page.)

Primary Examiner—James Housel
Assistant Examiner—Shanon Foley
(74) Attorney, Agent, or Firm—Morrison & Foerster, LLP

(57) ABSTRACT

Defined peptide subunits of *Streptococcus mutans* antigen I/II (SAI/II) are useful as agents to prevent and treat dental caries either by eliciting an immunological response or by preventing adhesion of *S. mutans* to the tooth.

25 Claims, 7 Drawing Sheets

OTHER PUBLICATIONS

Neutath et al., "Search for Hepatitis B. Virus Cell Receptors Reveals Binding Sites for Interleukin 6 on the Virus Envelope Protein," J Exp Med (1992) 4175:461–469.

Salgaller et al., "Generation of Specific Anti–Melanoma Reactivity by Stimulation of Human Tumor–Infiltrating Lymphocytes with MAGE–1 Synthetic Peptide," Cancer Immunol Immunother (1994) 105–116.

Sheriff et al., "Three Dimensional Structure of an Antibody–Antigen Complex," Proc Natl Acad Sci USA (1987) 84:8075–8079.

Simitsek et al., "Modulation of Antigen Processing by Bound Antibodies Can Boost or Suppress Class II Major Histocompatibility Complex Presentation of Different T Cell Determinants," J Exp Med (1995) 4181:1957–1963.

Smith–Gill et al., "Mapping the Antigenic Epitope for a Monoclonal Antibody Against Lysozyme," J Immunol (1982)125(1):314–322.

Steward et al., "Specificity of Antibodies Reactive with Hepatitis B Surface Antigen Following Immunization with Synthetic Peptides," Vaccine (1993) 11:1405–1414.

Todryk et al., "Induction of Immune Responses to Functional Determinants of a Cell Surface Streptococcal Antigen," Immunology (1996) 87:55–63.

Watts et al., "Suppressive Effect of Antibody on Processing of T Cell Epitopes," J Exp Med (1993) 4178:1459–1463.

* cited by examiner

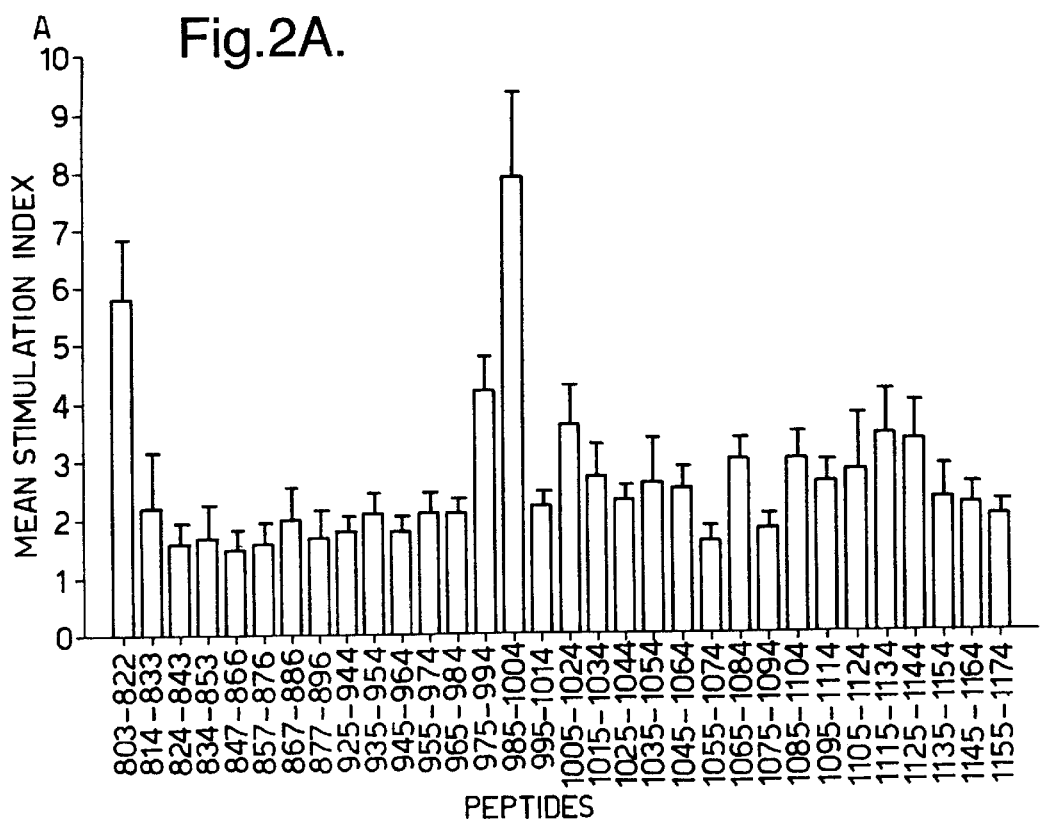
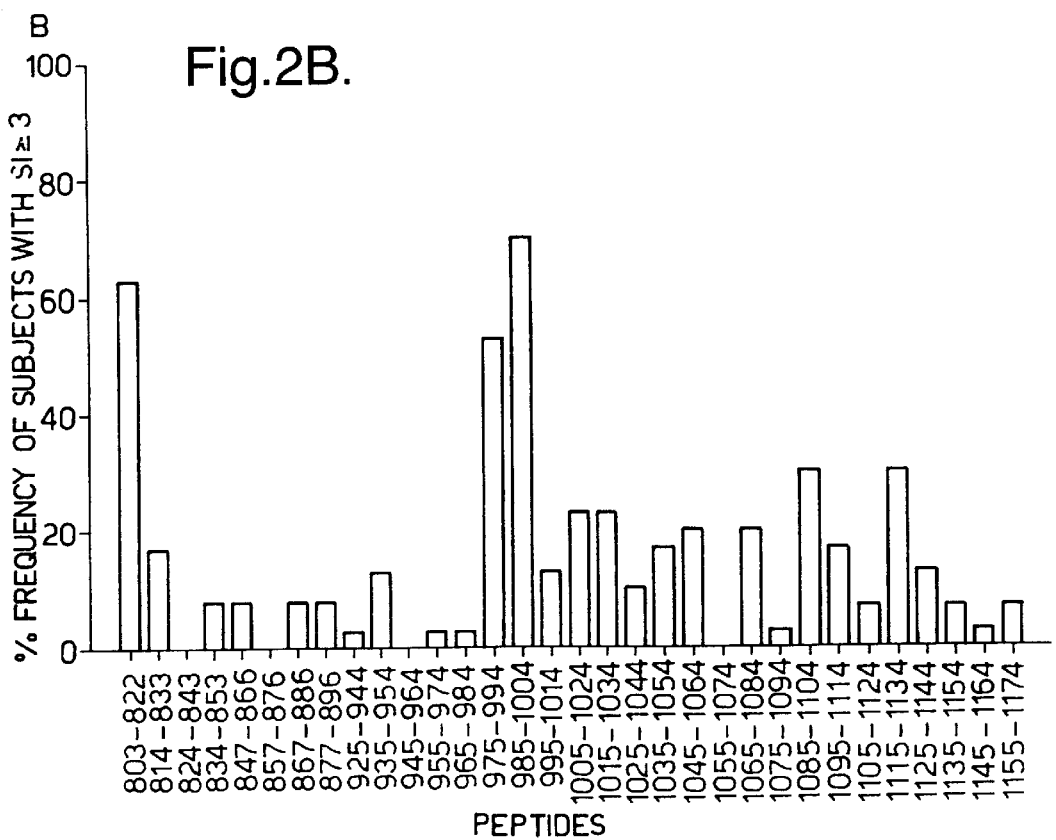

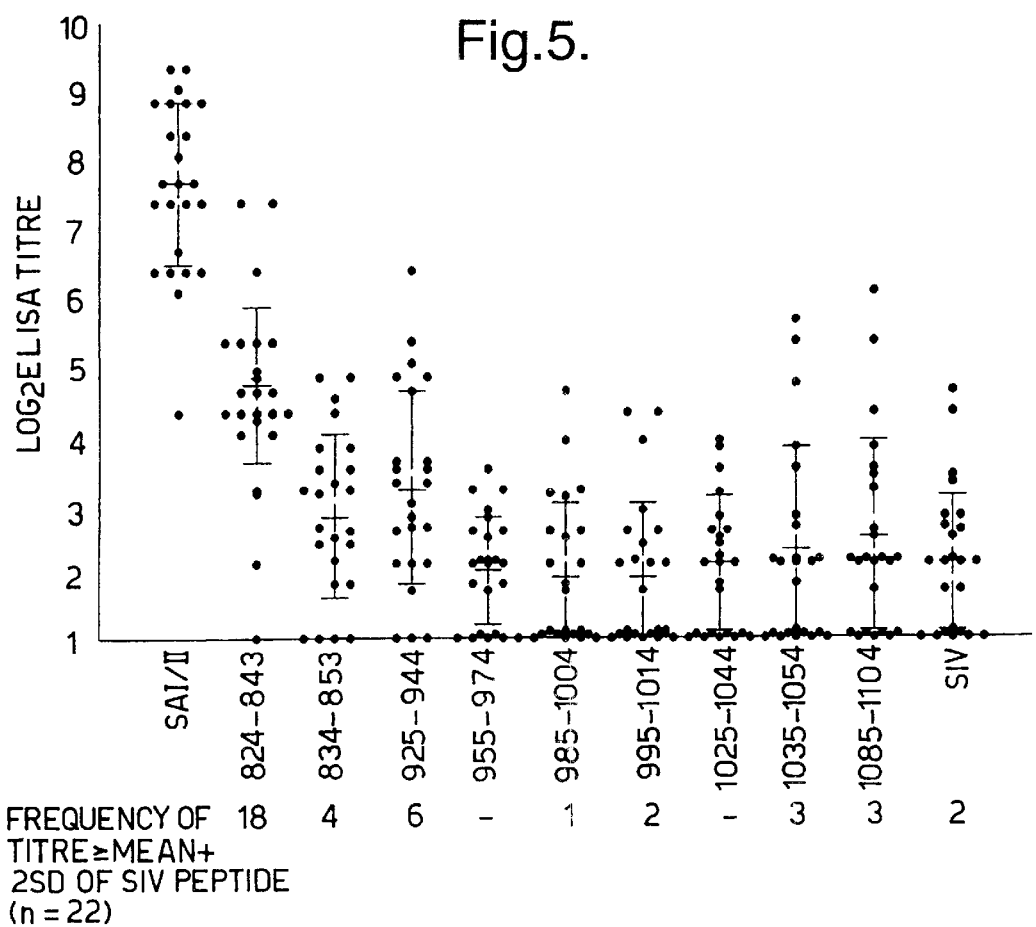
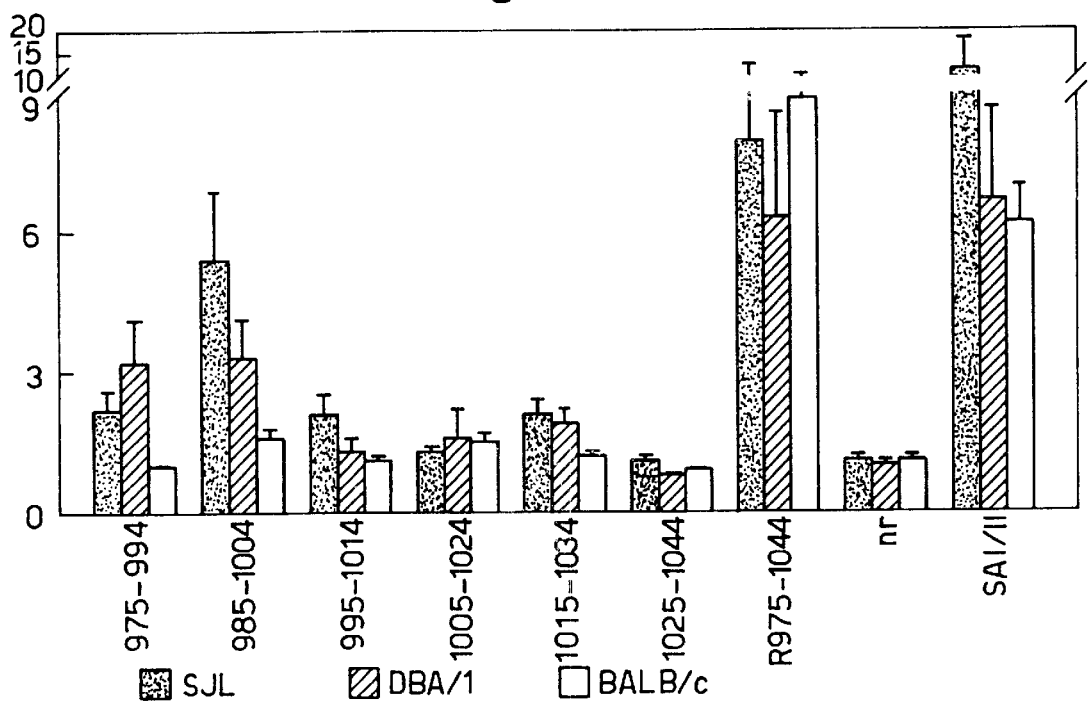

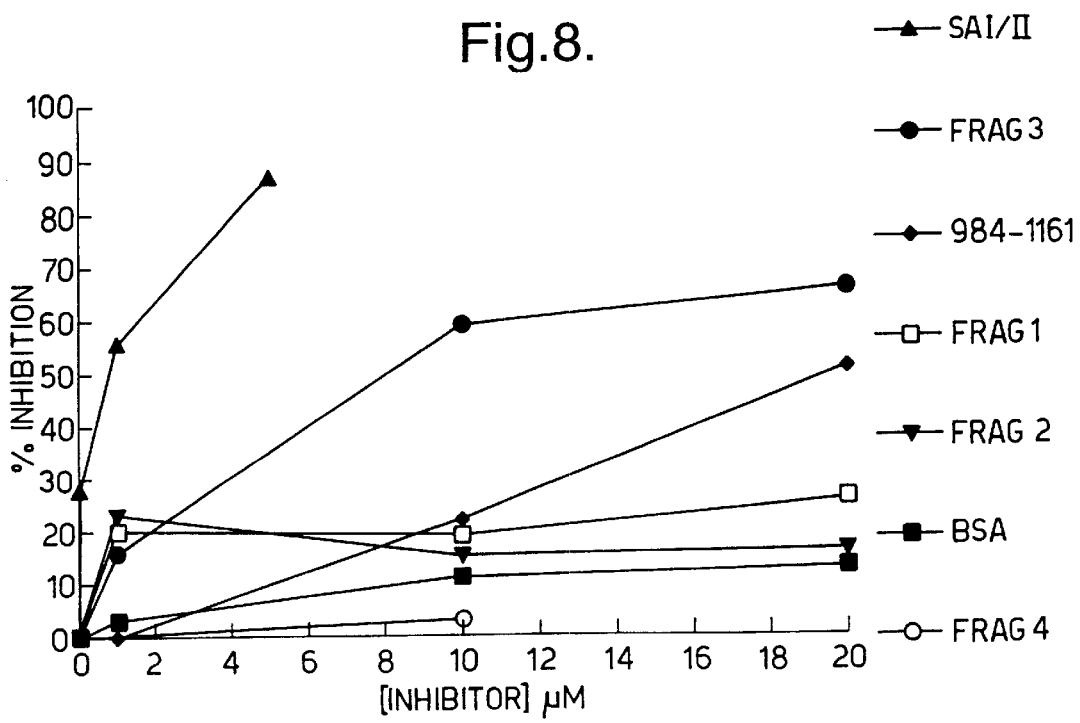
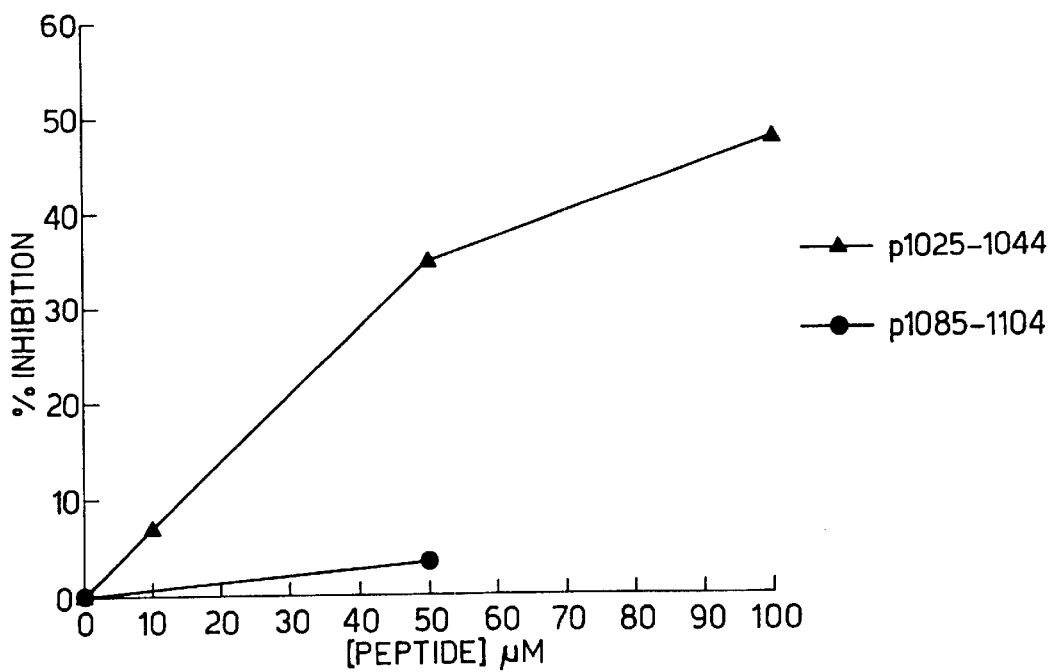

POLYPEPTIDE FRAGMENTS CAPABLE OF COMPETITION WITH *STREPTOCOCCUS MUTANS* ANTIGEN I/II

This application is a division of U.S. application Ser. No. 08/894,017, filed Oct. 20, 1997, now U.S. Pat. No. 6,024,958.

This invention relates to polypeptide fragments of the *Streptococcus mutans* I/II antigen that are useful in treating and preventing dental caries.

*Streptococcus mutans* is the main etiological agent of dental caries, a disease which affects mammals including humans.

The *S. mutans* I/II antigen (SA I/II) is a cell surface protein with an $M_r$ of about 185 kDa. It is believed to comprise several antigenic epitopes and to be at least partly responsible for *S. mutans* adhesion to teeth.

SA I/II is described in British Patent No. 2,060,647, as are number antibodies to it. A putative 3.5 to 4.5 kDa fragment of SA I/II, "antigen X", has also been described in European Patent No. 0 116 472.

However, it has now become clear that "antigen X" is not a fragment of SA I/II at all. Rather, it is a separate protein that merely co-purifies with SA I/II. It is believed to be encoded by a separate gene.

Two large fragments of SA I/II, an N-terminal fragment (residues 39 to 481) and a 40 kDa central fragment (residues 816 to 1213) are recognised by human serum antibodies. Within the central fragment, 80% of the sera tested recognise elements within a proline-rich region (residues 839–955) that comprises three tandem repeats. This suggests that this region includes one or more B-cell epitopes. The central fragment (residues 816–1213) is also believed to comprise one or more adhesion sites that mediate *S. mutans*' attachment to the tooth.

The aim of the above-mentioned work has been the development of vaccines for immunisation against dental caries. However, precise identification of the antigenic epitopes within SA I/II is a prerequisite for designing synthetic vaccines based on it. Similarly, precise identification of adhesion sites is essential for the design of drugs against dental caries that rely on inhibiting *S. mutans*' adhesion to the tooth.

No antigenic epitopes (T-cell or B-cell epitopes) or adhesion sites within SA I/II have been characterised, nor has the precise location of any such regions been suggested. Also, there has been no indication of the location of *S. mutans*' T-cell epitopes as the above-mentioned work has concentrated on *S. mutans*' ability to adhere to teeth and to generate a B-cell response.

The inventors have identified a number of T-cell epitopes, B-cell epitopes and adhesion sites within residues 803 to 1114 of SA I/II. Some of the T-cell and B-cell epitopes overlap or are contiguous with each other and/or with one or more of the adhesion sites.

The presence of a number of antigenic epitopes of both types and a number of adhesion sites within the same region of SA I/II could not have been predicted and the finding that some of the adhesion sites and epitopes overlap or are contiguous with each other is particularly surprising.

These findings make it possible to design effective synthetic vaccines against dental caries as well as drugs that engender resistance against the disease or alleviate pre-existing cases of it by preventing *S. mutans*' adhesion to the tooth. Further, the surprising finding that some of the T-antigenic epitopes and the adhesion site are contiguous or overlapping makes it possible to design bifunctional drugs that effect immunisation against dental caries as well as preventing adhesion of *S. mutans* to the tooth.

Accordingly, the present invention provides a nucleic acid sequence which codes upon expression in a prokaryoic or eukaryotic host cell for a polypeptide product having one or more properties selected from (i) the ability to adhere to a mammalian tooth in a competitive manner with naturally occurring *Streptococcus mutans* antigen I/II, thus preventing or diminishing the adhesion of *S.mutans* to the tooth; (ii) the ability to stimulate a T-cell response; and (iii) the ability to stimulate a B-cell response, said nucleic acid sequence being selected from:

(a) the sequences shown in SEQ. ID. Nos. 12 to 22 or the complementary strands thereof;

(b) nucleic acid sequences having a length of not more than 1000 base pairs which hybridise to the sequences defined in (a) over at least 70% of their length;

(c) nucleic acid sequences having a length of not more than 1000 base pairs which, but for the degeneracy of the genetic code, would hybridise to the nucleic acid sequences defined in (a) or (b) over at least 70% of their length and which sequences code for polypeptides having the same amino acid sequence code, would hybridise to the nucleic acid sequences defined in (a) or (b) over at least 70% of their length and which sequences code for polypeptides having the same amino acid sequence.

BRIEF DESCRIPTION OF THE DRAWINGS

FIG. 2. Proliferative responses to overlapping synthetic peptides ($20^{ers}$) of SA I/II.

a) Mean S.I. (±sem) of PBMC from 30 subjects. Mean cpm with medium only was 538±112.

b) Frequency of positive responses (S.I.≧3.0, cpm>500).

Figure 3:
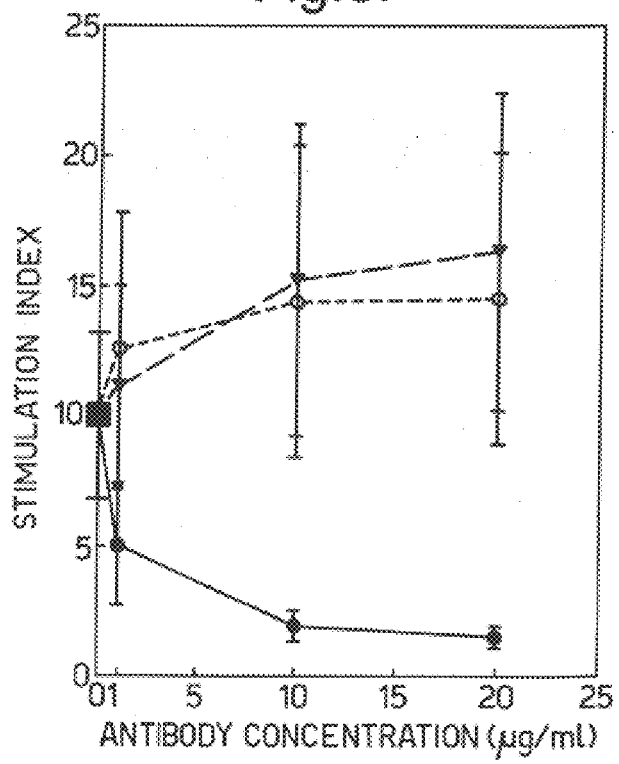

FIG. 3. MHC class II dependency of proliferative responses to SA I/II.

Figure 4:
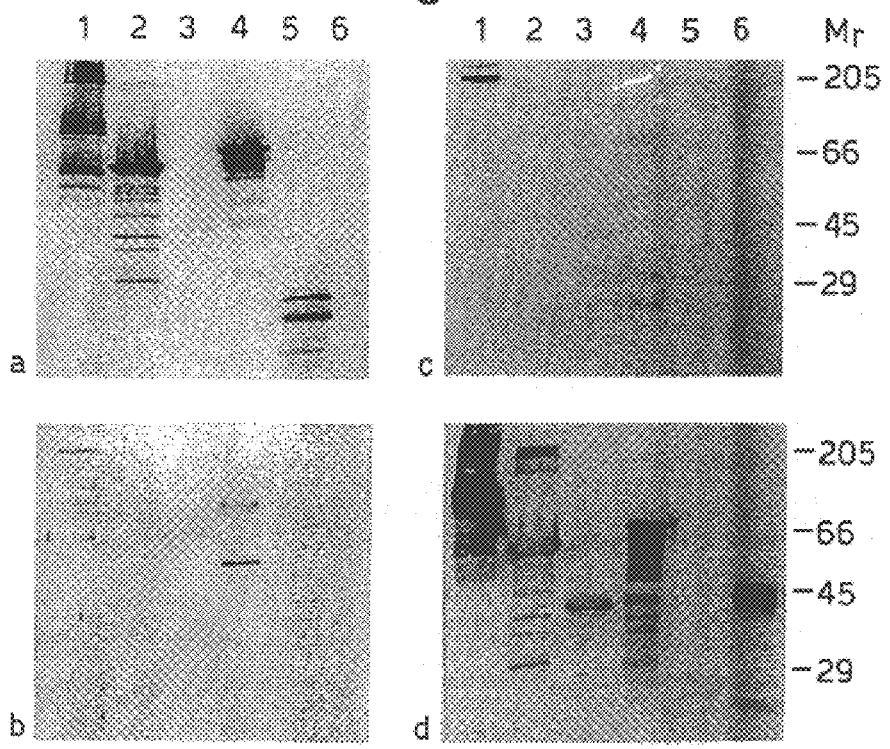

FIG. 4. Serum recognition of SA I/II and recombinant polypeptide fragments. Western blots from 3 subjects are shown (panels a–c) together with rabbit anti-SA I/II antiserum (panel d). Lanes, 1, SA I/II; lane 5, recombinant 984–1161.

FIG. 5. Human serum recognition of synthetic peptides of SA I/II.

a) Titres were determined by ELISA in 22 subjects to selected peptides of SA I/II and an irrelevant control peptide from SIVp27 (SIV). The frequencies of sera binding the peptides with a titre >mean+2S.D. the control peptide are also indicated.

Figure 6A:
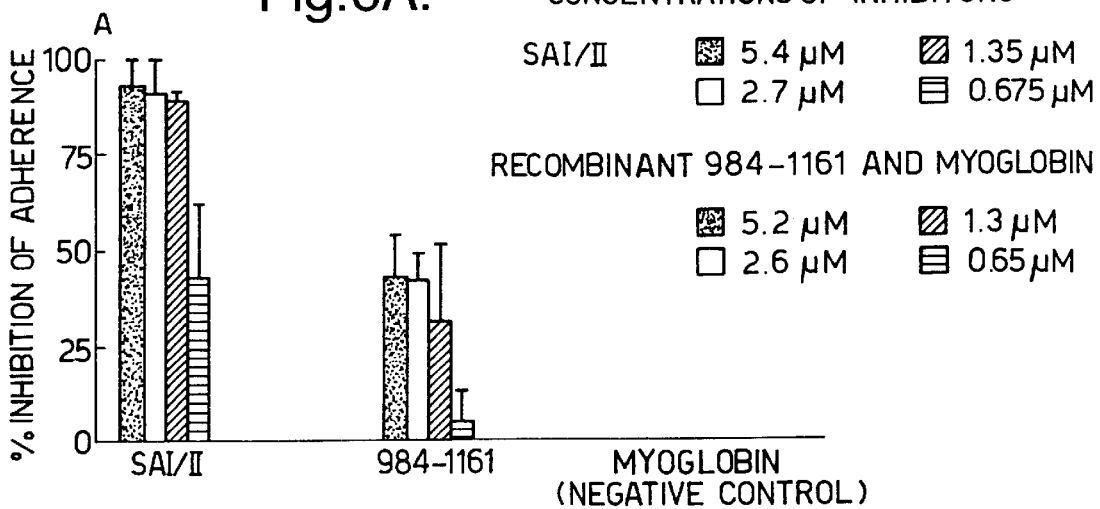
Figure 6B:
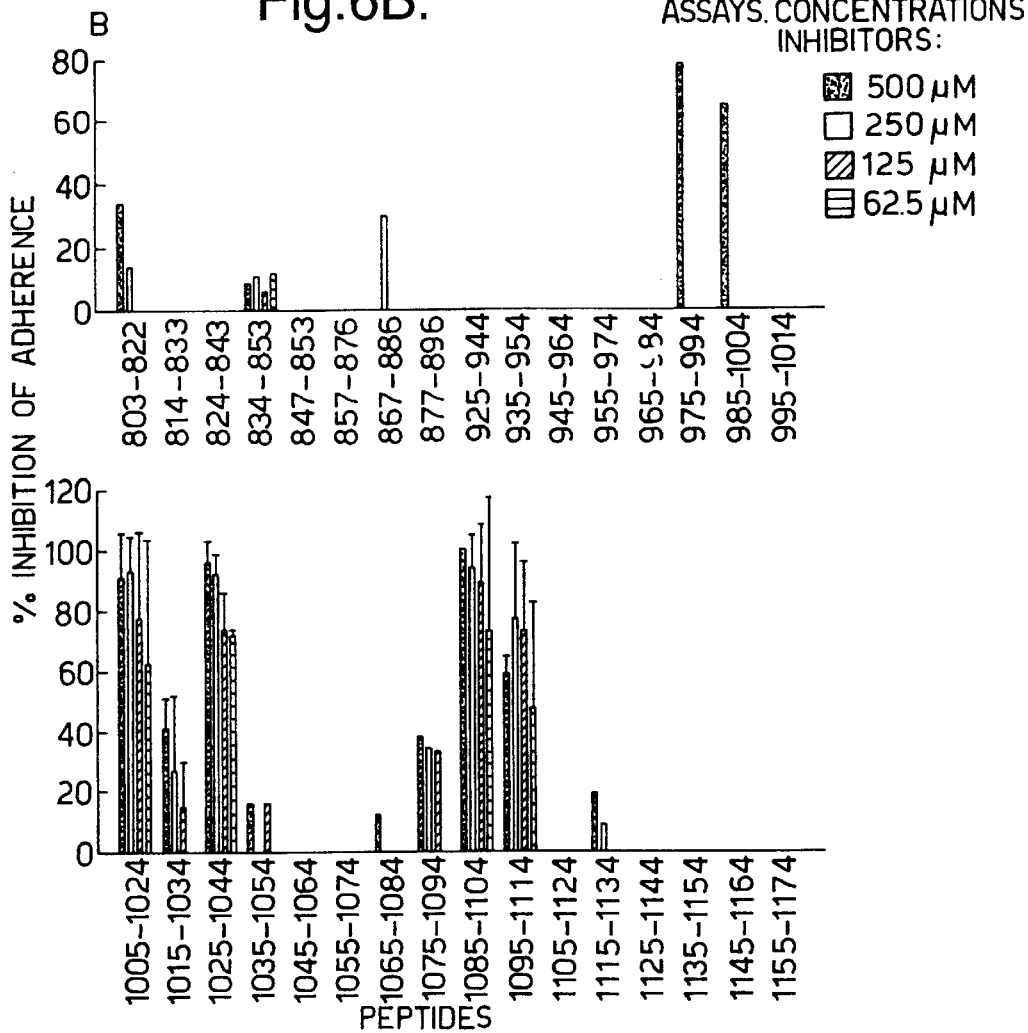

FIG. 6. Inhibition of adhesion of S. mutans.

a) SA I/II and recombinant fragment 984–1161.

b) Synthetic peptides.

FIG. 7. Proliferative responses of murine splenocytes following immunization with recombinant 975–1044 (SEQ. ID. No. 8).

FIG. 8. Competitive inhibition of SA I/II binding by various polypeptides.

FIG. 9. Dependence of competitive inhibition of SA I/II binding on concentration of two peptides.

Figure 10:
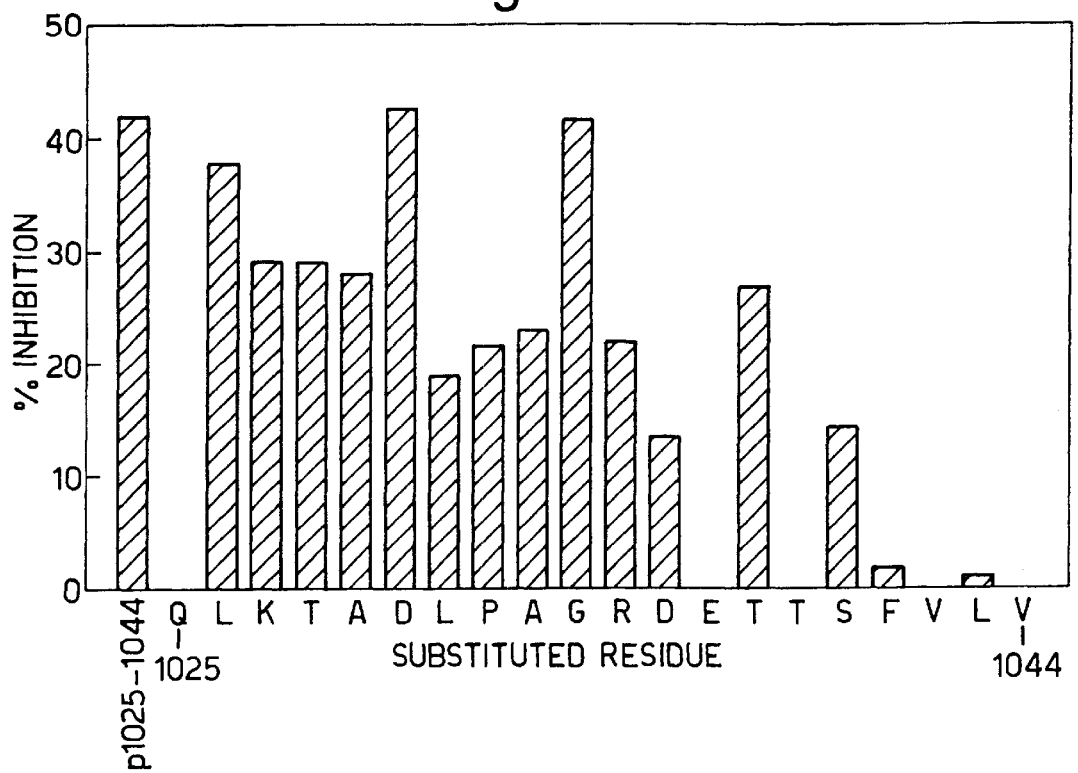

FIG. 10. Effects of substitution of certain residues on competitive inhibition.

Figure 11:
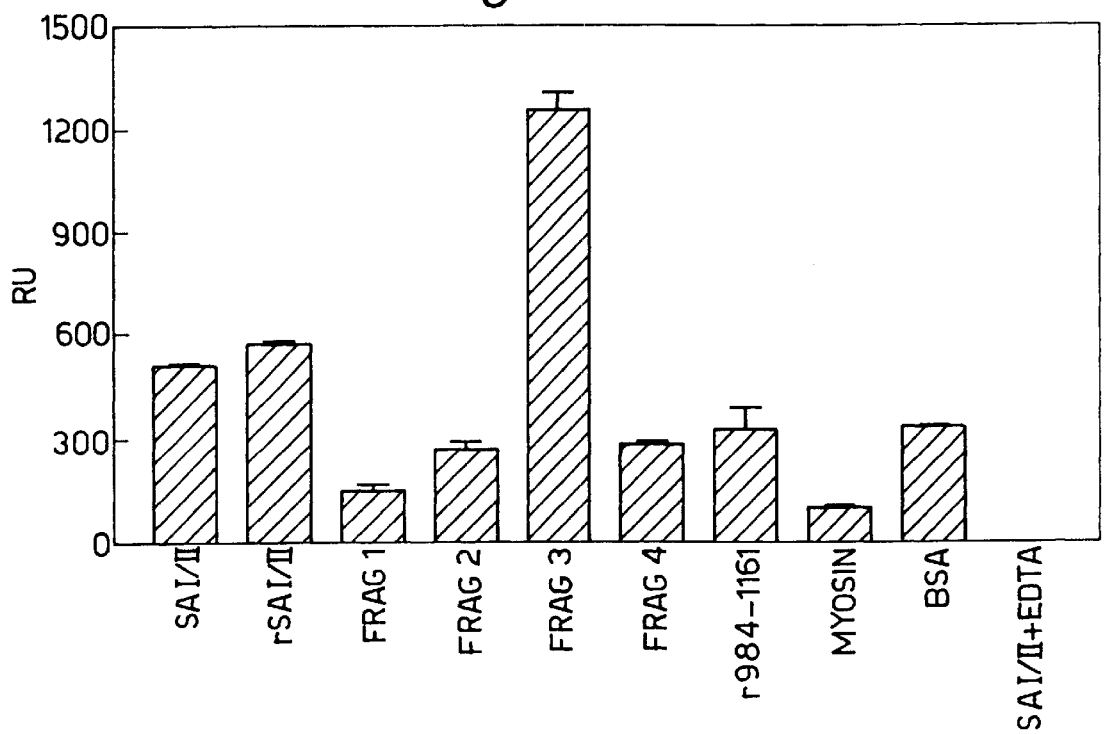

FIG. 11. Comparison of various recombinant polypeptides with respect to binding.

The polypeptides of the invention have one or more of the following properties. Firstly, they may have the ability to adhere to a mammalian tooth in a competitive manner with naturally occurring *Streptococcus mutans* antigen I/II, thus preventing or diminishing the adhesion of *S. mutans* to the tooth. Some of the peptides of the invention have been shown to inhibit adhesion of *S. mutans* to a tooth surface model (whole human saliva adsorbed to the wells of polystyrene microtitre plates or hydroxyapatite beads). Thus, these peptides comprise one or more adhesion sites and will adhere to a mammalian tooth in a competitive manner with naturally occurring SA I/II. Therefore, peptides according to the invention that comprise the adhesion site prevent or diminish the adhesion of *S. mutans* to the tooth. Peptides of the invention that comprise one or more adhesion epitopes include SEQ. ID. Nos. 1 to 6 and 8 to 10.

Secondly, peptides according to the invention may have the ability to stimulate a T-cell response. The inventors have shown that residues 803 to 854 and 925 to 1114 of SA I/II comprise a number of T-cell epitopes that are at least partially responsible for the T-cell response stimulated by the intact protein. Therefore, peptides according to the invention that comprise one or more of these the T-cell epitopes stimulate a T-cell response against *S. mutans* infection. Peptides of the invention that stimulate a T-cell response include those shown in SEQ ID Nos. 1 to 11.

Thirdly, the peptides of the invention may stimulate a B-cell response. The inventors have shown that residues 803 to 854 and 925 to 1114 of SA I/II comprise a number of B-cell epitopes and polypeptides according to the invention that comprise one or more B-cell epitopes stimulate a B-cell response against *S. mutans* infection. Peptides of the invention that comprise one or more B-cell epitopes include those shown in SEQ. ID. Nos. 1, 3 to 7 and 10.

The nucleic acid sequences of the present invention are preferably DNA, though they may be RNA. It will be obvious to those of skill in the art that, in RNA sequences according to the invention, the T residues shown in SEQ. ID. Nos. 12 to 22 will be replaced by U. Nucleic acid sequences of the invention will typically be in isolated or substantially isolated form. For example up to 80, up to 90, up to 95 or up to 100% of the nucleic acid material in a preparation of a nucleic acid of the invention will typically be nucleic acid according to the invention.

Some preferred nucleic acid sequences of the invention are those shown in SEQ. ID. Nos. 12 to 22. However, the nucleic acid sequences of the present invention are not limited to these sequences. Rather, the sequences of the invention include sequences that are closely related to these sequences and that encode a polypeptide having at least one of the biological properties of naturally occurring SA I/II. These sequences may be prepared by altering those of SEQ ID Nos. 12 to 22 by any conventional method, or isolated from any organism or made synthetically. Such alterations, isolations or syntheses may be performed by any conventional method, for example by the methods of Sambrook et al (Molecular Cloning: A Laboratory Manual; 1989).

For example, the sequences of the invention include sequences that are capable of selective hybridisation to those of SEQ. ID. Nos. 12 to 22 or the complementary strands thereof and that encode a polypeptide having one or more of the properties defined above. Such sequences capable of selectively hybridizing to the DNA of SEQ. ID. Nos. 12 to 22 will generally be at least 70%, preferably at least 80 or 90% and more preferably at least 95% homologous to the DNA of SEQ. ID. Nos. 12 to 22 over a region of at least 10, preferably at least 20, 30, 40, 50 or more contiguous nucleotides.

Such sequences that hybridise to those shown in SEQ. ID. Nos. 12 to 22 will typically be of similar size to them, though they may be longer or shorter. However, if they are longer, they may not simply encode large fragments of native SA I/II amino acid sequence. Thus, sequences that hybridise to those of SEQ. ID. Nos. 12 to 22 may be sequences of up to 1000 bases in length, for example up to 950 or up to 933 bases in length, 933 bases being the length of the DNA sequence encoding the largest specifically identified peptide of the invention (SEQ. ID. No. 21). Also, sequences that hybridise to those of SEQ. ID. Nos. 12 to 22 must do so over at least 50% of their length, for example up to 60%, up to 70%, up to 80%, up to 90%, up to 95%, or up to 99% of their length.

Such hybridisation may be carried out under any suitable conditions known in the art (see Sambrook et al (1989): Molecular Cloning: A Laboratory Manual). For example, if high stringency is required, suitable conditions include 0.2×SSC at 60° C. If lower stringency is required, suitable conditions include 2×SSC at 60° C.

Also included within the scope of the invention are sequences that differ from those defined above because of the degeneracy of the genetic code and encode the same polypeptide having one or more of the properties defined above, namely the polypeptide of SEQ. ID. Nos. 1 to 11 or a polypeptide related to one of these polypeptides in any of the ways defined below.

Thus, the nucleic acid sequences of the invention include sequences which, but for the degeneracy of the genetic code, would hybridise to those shown in SEQ. ID. Nos 12 to 22 or the complementary strands thereof. However, such sequences may not simply encode large fragments of native SA I/II amino acid sequences. Thus, these sequences may be up to 1000 bases in length, for example up to 950 or 933 bases in length. Also, their sequence must be such that, but of the degeneracy of the genetic code, they would hybridise to a sequence as shown in SEQ. ID. Nos. 12 to 22 over at least 50% of their length, for example, up to 60%, up to 70%, up to 80%, up to 90%, up to 95% or up to 99% of their length.

Also, the nucleic acid sequences of the invention include the complementary strands of the sequences defined above, for example the complementary strands of the nucleic acid sequences shown in SEQ. ID. Nos. 12 to 22.

Nucleic acid sequences of the invention will preferably be at least 30 bases in length, for example up to 50, up to 100, up to 200, up to 300, up to 400, up to 500, up to 600, up to 800 or up to 1000 bases.

Nucleic acid sequences of the invention may be extended at either or both of the 5' and 3' ends. Such extensions may be of any length. For example, an extension may comprise up to 10, up to 20, up to 50, up to 100, up to 200 or up to 500 or more nucleic acids. A 5' extension may have any sequence apart from that which is immediately 5' to the sequence of the invention (or the native sequence from which it is derived) in native SA I/II. A 3' extension may have any sequence apart from that which is 3' to the sequence of SEQ. ID. No. 13 in native SA I/II. Thus, the nucleic acid sequences of the invention may be extended at either or both of the 5' and 3' ends by any non-wild-type sequence.

The polypeptides of the invention are encoded by the DNA sequences described above. Thus, the polypeptides of the invention are not limited to the polypeptides of SEQ. ID. Nos. 1 to 11 although these sequences represent preferred polypeptides. Rather, the polypeptides of the invention also include polypeptides with sequences closely related to those of SEQ. ID. Nos. 1 to 11 that have one or more of the biological properties of SA I/II. These sequences may be prepared by altering those of SEQ ID Nos. 1 to 11 by any conventional method, or isolated from any organism or made synthetically. Such alterations, isolations or syntheses may be performed by any conventional method, for example by the methods of Sambrock et al (Molecular Cloning: A Laboratory Manual; 1989). In particular, polypeptides related to those of SEQ ID Nos. 1 to 11 may be prepared by modifying DNA sequences as shown in SEQ ID Nos. 12 to 22 expressing them recombinantly.

The polypeptides of the invention may be encoded by nucleic acid sequences that have less than 100% sequence identity with those of SEQ. ID. Nos. 12 to 22. Thus, polypeptides of the invention may include substitutions, deletions, or insertions, that distinguish them from SEQ. ID. Nos. 1 to 11 as long as these do not destroy the biological property or properties that the polypeptides have in common with SA I/II.

A substitution, deletion or insertion may suitably involve one or more amino acids, typically from one to five, one to ten or one to twenty amino acids, for example, a substitution, deletion or insertion of one, two, three, four, five, eight, ten, fifteen, or twenty amino acids. Typically, a polypeptide of the invention has at least 60%, at least 80%, at least 90%, or at least 95% sequence identity to the sequence of any one of SEQ. ID. Nos. 1 to 11.

In general, the physicochemical nature of the sequence of SEQ. ID. Nos. 1 to 11 should be preserved in a polypeptide of the invention. Such sequences will generally be similar in charge, hydrophobicity and size to that of SEQ. ID. Nos. 1 to 11. Examples of substitutions that do not greatly affect the physicochemical nature of amino acid sequences are those in which an amino acid from one of the following groups is substituted by a different amino acid from the same group:

H, R and K

I, L, V and M

A, G, S and T

D, E, Q and N.

However, it may be desirable to alter the physicochemical nature of the sequence of SEQ. ID. Nos. 1 to 11 in order to increase its therapeutic effectiveness. For example, many of the amino acids in the polypeptides of the invention are acidic. For example, residues 975 to 1044 (SEQ. ID. No. 8) as a whole are of an acidic nature. This acidity is believed to facilitate binding to a mammalian tooth. Thus, it may be desirable to increase the acidity of polypeptides of the invention by adding acidic residues or by substituting acidic residues for non-acidic ones. Acidic residues include aspartic acid and glutamic acid.

Where polypeptides of the invention are synthesised chemically, D-amino acids (which do not occur in nature) may be incorporated into the amino acid sequence at sites where they do not affect the polypeptides biological properties. This reduces the polypeptides' susceptibility to proteolysis by the recipient's proteases.

The nucleic acid sequences encoding the polypeptides of the invention may be extended at one or both ends by any non-wild-type sequence.

Thus, the polypeptides of the invention may be extended at either or both of the C- and N-termini by an amino acid sequence of any length. For example, an extension may comprise up to 5, up to 10, up to 20, up to 50, or up to 100 or 200 or more amino acids. An N-terminal extension may have any sequence apart from that which is N-terminal to the sequence of SEQ. ID. No. the invention (or the native sequence from which it is derived) in native SA I/II. A C-terminal extension may have any sequence apart from that which is C-terminal to the sequence of the invention (or the native sequence from which it is derived) in native SA I/II. Thus, the polypeptides of the invention may be extended at either or both of the C- and N-termini by any non-wild-type sequence.

The polypeptides of the invention may be attached to other polypeptides or proteins that enhance their antigenic properties. Thus, polypeptides of the invention may be attached to one or more other antigenic polypeptides. These additional antigenic polypeptides may be derived from *S. mutans* or from another organism. Possible additional antigenic polypeptides include heterologous T-cell epitopes derived from other *S. mutans* proteins or from species other than *S. mutans*. Heterologous B-cell epitopes may also be used. Such heterologous T-cell and or B-cell epitopes may be of any length and epitopes of up to 5, up to 10 or up to 20 amino acids in length are particularly preferred. These additional antigenic polypeptides may be attached to the polypeptides of the invention chemically. Alternatively, one or more additional antigenic sequences may comprise an extension to a polypeptide of the invention.

A polypeptide of the invention may be subjected to one or more chemical modifications, such as glycosylation, sulphation, COOH-amidation or acylation. In particular, polypeptides that are acetylated at the N-terminus are preferred, as are polypeptides having C-terminal amide groups. Preferred polypeptides may have one or more of these modifications. For example, particularly preferred peptides may have a C-terminal amide group and N-terminal acetylation.

A polypeptide of the invention may form part of a larger polypeptide comprising multiple copies of the sequence of one or more of SEQ. ID. Nos. 1 to 11 or a sequences related to them in any of the ways defined herein.

Polypeptides of the invention typically comprise at least 15 amino acids, for example 15 to 20, 20 to 50, 50 to 100 or 100 to 200 or 200 to 300 amino acids. Preferred polypeptides include those shown in SEQ. ID. Nos. 1 to 11.

Polypeptides according to the invention may be purified or substantially purified. Such a polypeptide in substantially purified form will generally form part of a preparation in which more than 90%, for example up to 95%, up to 98% or up to 99% of the peptide material in the preparation is that of a polypeptide or polypeptides according to the invention.

The nucleic acid sequences and polypeptides of the invention were originally derived from *S. mutans*. However, nucleic acid sequences and/or polypeptides of the invention may also be obtained from other organisms, typically bacteria, especially other streptococci. They may be obtained either by conventional cloning techniques or by probing genomic or cDNA libraries with nucleic acid sequences according to the invention. This can be done by any conventional method, such as the methods of Sambrook et al (Molecular Cloning: A Laboratory Manual; 1989).

A nucleic acid sequence according to the invention may be included within a vector, suitably a replicable vector, for instance a replicable expression vector.

A replicable expression vector comprises an origin of replication so that the vector can be replicated in a host cell such as a bacterial host cell. A suitable vector will also typically comprise the following elements, usually in a 5' to 3' arrangement: a promoter for directing expression of the nucleic acid sequence and optionally a regulator of the promoter, a translational start codon anct a nucleic acid sequence according to the invention encoding a polypeptide having one or more of the biological properties of SA I/II.

A non-replicable vector lacks a suitable origin at replication whilst a non-expression vector lacks an effective promoter.

The vector may also contain one or more selectable marker genes, for example an ampicillin resistance gene for the identification of bacterial transformants. One particular preferred marker gene is the kanamycin resistance gene. Optionally, the vector may also comprise an enhancer for the promoter. If it is desired to express the nucleic acid sequence of the invention in a eucaryotic cell, the vector may also comprise a polyadenylation signal operably linked 3' to the nucleic acid encoding the functional protein. The vector may also comprise a transcriptional terminator 3' to the sequence encoding the polypeptide of the invention.

The vector may also comprise one or more non-coding sequences 3' to the sequence encoding the polypeptide of the invention. These may be from S. mutans (the organism from which the sequences of the invention are derived) or the host organism which is to be transformed with the vector or from another organism.

In an expression vector, the nucleic acid sequence of the invention is operably linked to a promoter capable of expressing the sequence. "Operably linked" refers to a Juxtaposition wherein the promoter and the nucleic acid sequence encoding the polypeptide of the invention are in a relationship permitting the coding sequence to be expressed under the control of the promoter. Thus, there may be elements such as 5' non-coding sequence between the promoter and coding sequence. These elements may be native either to S. mutans or to the organism from which the promoter sequence is derived or to neither organism. Such sequences can be included in the vector if they enhance or do not impair the correct control of the coding sequence by the promoter.

The vector may be of any type. The vector may be in linear or circular form. For example, the vector may be a plasmid vector. Those of skill in the art will be able to prepare suitable vectors comprising nucleic acid sequences encoding polypeptides of the invention starting with widely available vectors which will be modified by genetic engineering techniques such as those described by Sambrook et al (Molecular Cloning: A Laboratory Manual; 1989). Preferred starting vectors include plasmids that confer kanamycin resistance and direct expression of the polypeptide of the invention via a tac promoter.

In an expression vector, any promoter capable of directing expression of a sequence of the invention in a host cell may be operably linked to the nucleic acid sequence of the invention. Suitable promoters include the tac promoter.

Such vectors may be used to transfect or transform a host cell. Depending on the type of vector, they may be used as cloning vectors to amplify DNA sequences according to the invention or to express this DNA in a host cell.

A further embodiment of the invention provides host cells harbouring vectors of the invention, i.e. cells transformed or transfected with vectors for the replication and/or expression of nucleic acid sequences according to the invention, including the sequences shown in SEQ. ID. Nos. 12 to 22. The cells will be chosen to be compatible with the vector and may for example be bacterial cells.

Transformed or transfected bacterial cells, for example E.coli cells, will be particularly useful for amplifying nucleic acid sequences of the invention as well as for expressing them as polypeptides.

The cells may be transformed or transfected by any suitable method, such as the methods described by Sambrook et al (Molecular cloning: A Laboratory Manual; 1989). For example, vectors comprising nucleic acid sequences according to the invention may be packaged into infectious viral particles, such as retroviral particles. The constructs may also be introduced, for example, by electroporation, calcium phosphate precipitation, biolistic methods or by contacting naked nucleic acid vectors with the cells in solution.

In the said nucleic acid vectors with which the host cells are transformed or transfected, the nucleic may be DNA or RNA, preferably DNA.

The vectors with which the host cells are transformed or transfected may be of any suitable type. The vectors may be able to effect integration of nucleic acid sequences of the invention into the host cell genome or they may remain free in the cytoplasm. For example, the vector used for transformation may be an expression vector as defined herein.

The present invention also provides a process of producing polypeptides according to the invention. Such a process will typically comprise transforming or transfecting host cells with vectors comprising nucleic acid sequences according to the invention and expressing the nucleic acid sequence in these cells. In this case, the nucleic acid sequence will be operably linked to a promoter capable of directing its expression in the host cell. Desirably, such a promoter will be a "strong" promoter capable of achieving high levels of expression in the host cell. It may be desirable to overexpress the polypeptide according to the invention in the host cell. Suitable host cells for this purpose include yeast cells and bacterial cells, for example E. coli cells, a particularly preferred E. coli strain being E. coli K12 strain BL 21. However, other expression systems can also be used, for example baculovirus systems in which the vector is a baculovirus having in its genome nucleic acid encoding a polypeptide of the invention and expression occurs when the baculovirus is allowed to infect insect cells.

The thus produced polypeptide of the invention may he recovered by any suitable method known in the art. Optionally, the thus recovered polypeptide may be purified by any suitable method, for example a method according to Sambrook et al (Molecular Cloning: A Laboratory Manual).

The polypeptides of the invention may also be synthesised chemically using standard techniques of peptide synthesis. For shorter polypeptides, chemical synthesis may be preferable to recombinant expression. In particular, peptides of up to 20 or up to 40 amino acid residues in length may desirably be synthesised chemically.

The nucleic acid sequences of the invention may be used to prepare probes and primers. These will be useful, for example, in the isolation of genes having sequences similar to that of SEQ. ID. No. 24. Such probes and primers may be of any suitable length, desirably from 10 to 100, for example from 10 to 20, 20 to 50 or 50 to 100 bases in length.

The present invention also provides antibodies to the polypeptides of the invention. These antibodies may be monoclonal or polyclonal. For the purposes of this invention, the term "antibody", includes fragments of whole. antibodies which retain their binding activity for a target antigen. Such fragments include Fv, F(ab') and F(ab')$_2$ fragments, as well as single chain antibodies.

The antibodies may be produced by any method known in the art, such as the methods of Sambrook et al (Molecular Cloning: A Laboratory Manual; 1989). For example, they may be prepared by conventional hybridoma techniques or, in the case of modified antibodies or fragments, by recombinant DNA technology, for example by the expression in a suitable host vector of a DNA construct encoding the modified antibody or fragment operably linked to a promoter. Suitable host cells include bacterial (for example E.

coli), yeast, insect and mammalian cells. Polyclonal antibodies may also be prepared by conventional means which comprise inoculating a host animal, for example a rat or a rabbit, with a peptide of the invention and recovering immune serum.

The present invention also provides pharmaceutical compositions comprising polypeptides of the invention. Three types of pharmaceutical compositions are particularly preferred. Firstly, compositions comprising polypeptides of the invention that include T-cell and/or B-cell epitopes may be used as vaccines against dental caries. Secondly, compositions comprising polypeptides of the invention that comprise adhesion sites will prevent or diminish adhesion of S. mutans to the tooth and can be used in the treatment of pre-existing cases of dental caries. Thirdly, compositions comprising polypeptides of the invention that include both one or more antigenic (T-cell or B-cell) epitopes and one or more adhesion epitopes can be used to effect vaccination against dental caries at the same time as caring pre-existing cases of the disease. A similar effect can be achieved by including in a composition one or more peptides comprising one or more antigenic epitopes and one or more peptides comprising one or more adhesion sites.

A range of mammalian species can be vaccinated against dental caries using the polypeptides of the invention. Vaccination of humans is particularly desirable.

The compositions of the invention may be administered to mammals including humans by any route appropriate. Suitable routes include topical application in the mouth, oral delivery by means of tablets or capsule and parenteral delivery, including subcutaneous, intramuscular, intravenous and intradermal delivery. Preferred routes of administration are topical application in the mouth and injection, typically subcutaneous or intramuscular injection, with a view to effecting systemic immunisation.

As previously indicated, polypeptides according to the invention may also be mixed with other antigens of different immunogenicity.

The compositions of the invention may be administered to the subject alone or in a liposome or associated with other delivery molecules. The effective dosage depends on many factors, such as whether a delivery molecule is used, the route of delivery and the size of the mammal being vaccinated. Typical doses are from 0.1 to 100 mg of the polypeptide of the invention per dose, for example 0.1 to 1 mg, and 1 to 5 mg, 5 to 10 mg and 10 to 100 mg per dose. Doses of from 1 to 5 mg are preferred.

Dosage schedules will vary according to, for example, the route of administration, the species of the recipient and the condition of the recipient. However, single doses and multiple doses spread over periods of days, weeks or months are envisaged. A regime for administering a vaccine composition of the invention to young human patients will conveniently be:6 months, 2 years, 5 years and 10 years, with the initial dose being accompanied by adjuvant and the subsequent doses being about ½ to ¼ the level of polypeptide in the initial dose. The frequency of administration can, however, be determined by monitoring the antibody levels in the patient.

Where the peptides of the invention are to be applied topically in the mouth, one preferred dosage regime is to apply one or more polypeptides of the invention on two or more occasions, for example 2 to 10 occasions over a period of a few weeks, for example one to six weeks. A particularly preferred regime of this type involves six applications of a polypeptide of the invention over a period of three weeks.

Typical doses for each topical application are in the range of 0.1 to 100 mg for example 0.1 to 1 mg, 1 to 10 mg and 10 to 100 mg. Doses of from 1 to 5 mg for each application are preferred.

While it is possible for polypeptides of the invention to be administered alone it is preferable to present them as pharmaceutical formulations. The formulations of the present invention comprise at least one active ingredient, a polypeptide of the invention, together with one or more acceptable carriers thereof and optionally other therapeutic ingredients. The carrier or carriers must be "acceptable" in the sense of being compatible with the other ingredients of the formulation and not deleterious to the recipients thereof, for example, liposomes.

Formulations suitable for parenteral administration include aqueous and non-aqueous sterile injection solutions which may contain anti-oxidants, buffers, bacteriostatis, bactericidal antibiotics and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs.

In particular, the polypeptides of the invention may be coupled to lipids or carbohydrates. This increases their ability to adhere to teeth, either by prolonging the duration of the adhesion or increasing its affinity, or both. This is particularly desirable for shorter polypeptides of the invention, which comprise up to around 40 amino acid residues.

Of the possible formulations, sterile pyrogen-free aqueous and non-aqueous solutions are preferred. Also preferred are formulations in which the polypeptides of the invention are contained in liposomes. Injection solutions and suspensions may be prepared extemporaneously from sterile powders, granules and tablets of the kind previously described.

Oral methods of administration may produce an effect systemically or locally in the mouth. Orally active preparations can be formulated in any suitable carrier, such as a gel, toothpaste, mouthwash or chewing gum.

It should be understood that in addition to the ingredients particularly mentioned above the formulations of this invention may include other agents conventional in the art having regard to the type of formulation in question.

Accordingly, the present invention provides a method of vaccinating a mammalian host against dental caries or treating dental caries, which method comprises administering to the host an effective amount of a pharmaceutical composition as described above, for example a vaccine composition.

Antibodies, including monoclonal antibodies, can be formulated for passive immunisation as indicated above for the formulation of including polypeptides of the invention. Preferred formulations for passive immunisation include solid or liquid formulations such as gels, toothpastes, mouthwashes or chewing gum.

A further aspect of the present invention is a naked nucleic acid vaccine. In this embodiment, the vaccine composition comprises a nucleic acid, typically an isolated nucleic acid, preferably DNA, rather than a polypeptide. The nucleic acid is injected in to a mammalian host and expressed in vivo, generating a polypeptide of the invention. This stimulates a T-cell response, which leads to protective immunity against dental caries in the same way as direct vaccination with a polypeptide of the invention.

Naked nucleic acid vaccination can be carried out with any nucleic acid according to the invention as long as it encodes a polypeptide that stimulates a T-cell and or B-cell response. Preferred nucleic acids are those shown in SEQ. ID Nos. 1 to 11. These will typically be included within an expression vectors as defined above. In such an expression vector, the nucleic acid according to the invention will typically be operably linked to a promoter capable of directing its expression in a mammalian host cell. For example, promoters from viral genes that are expressed in the mammalian cells such as the cytomegalovirus (CMV) immediate early gene promoter are suitable. Also suitable are promoters from mammalian genes that are expressed in many or all mammalian cell types such as the promoters of "housekeeping" genes. One such promoter is the p-hydroxymethyl-CoA-reductase (HMG) promoter (Gautier et al (1989): Nucleic Acids Research; 17, 8839).

For naked nucleic acid vaccination, it is preferred that the nucleic acid sequence according to the invention is incorporated into a plasmid vector, since it has been found that covalent closed circle (CCC) plasmid DNA can be taken up directly by muscle cells and expressed without being integrated into the cells' genomic DNA (Ascadi et al (1991): The New Biologist; 3, 71–81). Naked nucleic acid vaccine may be prepared as any of the types of formulation mentioned above in respect of conventional polypeptide-based vaccines. However, formulations suitable for parenteral injection, especially intramuscular injection, are preferred. Naked nucleic acid vaccines may be delivered in any of the ways mentioned above in respect of conventional polypeptide-based vaccines but intramuscular injection is preferred.

Accordingly, the present invention provides a vaccine composition comprising a nucleic acid sequence or vector as described above and an acceptable carrier.

The following examples illustrate the invention.

EXAMPLES

Materials and Methods

Materials. Fmoc amino acids, benzotriazole-1-yl-oxytris-pyrrolidino-phosphonium hexaf lurophosphate (PyBOP) and Rink Amide MBHA resin were purchased from Calbiochem-Novabiochem (UK) Ltd., (Nottingham, UK). Dimethylformamide, trifluoroacetic acid, diethyl ether, dichloromethane and piperidene were purchased from Romil Chemicals Ltd (Loughborough, UK). Di-isopropylethylamine was from Aldrich Chemical Co. (Dorset, UK). Oligonucleotides were purchased from Oswel DNA Service (University of Edinburgh, Edinburgh, UK).

Bacteria and Growth Conditions

S.mutans Guy's strain (serotype c) were grown in 10 L basal medium supplemented as described previously (Russel et al (1978) : Arch. Oral Biol., 2317; Russel et al (1980): Infect, Immun. 61, 5490) at 37° C. for 72 h for SA I/II preparation. For the adhesion assay, S. mutans were grown in Todd-Hewitt broth (Difco Laboratories, Detroit, Mich.). Escherichia coli BL21 (DE3) (Novagen Inc., Madison, wis.) harbouring pET15b were grown at 37° C. in Luria-Bertani broth supplemented with carbenicillin (50 μg/ml) and recombinant protein expression was induced with isoppropyl-β-D-thiogalactopryanoside (1 mM).

Antigens. SA I/II was prepared from S. mutans (serotype c, Guy's strain) as described by Russel et al (1980: Infect. Immun. 28, 486). Using the procedure of Munro et al (1993: Infect. Immun. 61, 4590), the portion of the gene encoding residues 984–1161 was amplified by using the oligonucleotide primers: (5') ATACATATGCCAACTGTTCATTTC-CATTACTTT (SEQ. ID. No. 25) and (3') GCCATTGTC-GACTCATTCATTTTTATTAACCTTAGT (SEQ. ID. No. 26), cloned into pET15b (modified by the addition of a Sal I site) and expressed in E. coli.

Synthetic peptides. Peptide amides (20 mers overlapping by 10 residues) were synthesised on Rink amide MBHA resin in sealed porous polypropylene bags by the manual simultaneous multiple peptide synthesis procedure (Houghten (1985) PNAS 892, 5131) using Fmoc chemistry. PyBOP was used as coupling agent and Fmoc amino acids were activated in situ by addition of diisopropylethylamine. Following 20 cycles of synthesis, resin was washed with dimethylformamide followed by dichloromethane and peptides were cleaved by incubation in trifluoroacetic acid-ethanedithiol-anisole-phenol-$H_2O$ (82.5:2.5:5:5:5; v/v/v/w/v) for 2 h at room temperature. Peptides were precipitated by the addition of 5 volumes ether, recovered by centrifugation and washed three times with ether. Finally, peptides were dissolved in water and lyophilised. The scale of synthesis was 50 μmol. Aliquots of each peptide were hydrolysed in 6M HCl at 110° C. for 24 h and compositions were determined using the Beckman 121 MB automated analyser (Beckman Instruments Ltd, Bucks, UK). In each case the composition matched that predicted.

Antibodies. MAbs, L243 (anti-MHC class II) and W6/32 (anti-MHC class I) were produced from cultures of hybridomas obtained from the American Type Culture Collection (Rockville, Md., USA). ID4 an isotype (IgG2a) matched control of irrelevant specificity was provided by Dr. P. Shepherd (Department of Immunology, UMDS, Guys Hospital, London, UK). Rabbit anti-SA I/II antiserum was prepared as described previously (Russel et al (1980). Infect. Immun. 28, 486).

Lymphoproliferative assay. Defibrinated blood from volunteers was separated on a Ficoll gradient. Sera was used for antibody assays (see below) while peripheral blood mononuclear cells (PBMCs) were washed and resuspended in RPMI 1640 (Sigma Chemical Co., St. Louis, Mo., USA) supplemented with 2 mM L-glutamine, penicillin (100 IU/ml), streptomycin sulphate (100 μg/ml) and 10% heat-inactivated autologous serum. PBMCs ($10^5$ cells/well) were cultured in 96-well round-bottomed plates (Costar, Cambridge, Mo., USA) in a total volume of 200 μl. Three replicates of each culture were incubated with three concentrations (1, 10 and 40 μg/ml) of SA I/II, recombinant fragments, non-recombinant control or synthetic peptides. Incubation was at 37° C. in a humidified atmosphere with 5% $CO_2$ for 6 days. Each culture received 0.2 μCi (7.4 kBq) of [$^3$H]-thymidine (Amersham International, Bucks, UK) 6h before harvesting. Cultures were harvested onto glass fibre filters using a Dynatech (Chantilly, Va., USA) Minimal Cell harvester and [$^3$H]-thymidine incorporation was measured using the LKB liquid scintillation counter (Bromma, Sweden). Proliferation was expressed as stimulation index which is mean counts per minute (cpm) of antigen-stimulated, divided by cpm of antigen-free cultures. Concanavalin A (10 μg/ml) (Sigma Chemical Co., St. Louis, Mo., USA) was used with every culture as a positive control but the results are not presented.

MHC dependency of proliferative responses to SA I/II was determined by culturing cells with antigen (10 μg/ml) as above in the presence of MAbs L235, W6/32 or ID4 at 1, 10 and 20 μg/ml. Cultures were incubated with [3H]-thymidine, harvested and [$^3$H]-thymidine uptake was determined as described above.

ELISA for serum antibodies. Antibody recognition of synthetic peptides was determined by ELISA. Peptides (10 μg/ml) in phosphate buffered saline (PBS) were adsorbed to wells of polystyrene microtitre plates (Dynatech) for 2h at room temperature. Plates were washed and wells were treated with 1.5% (w/v) bovine serum albumen (BSA) for 1 h at room temperature to block unbound sites. After washing, bound peptides were incubated with serially diluted sera in duplicate. Bound IgG antibodies were determined by incubation with alkaline phosphate conjugated-goat anti-human Ig (Sigma Chemical Co.) and subsequent reaction with paranitrophenyl phosphate (Sigma Chemical Co.). Plates were read at 405 nm using the microplate reader model 450 (Bio-Rad). After initial screening, the assay was repeated at least 3 times with each serum using a restricted set of peptides. SA I/II (2 µg/ml) was included in each assay as was an irrelevant peptide (HQAAMQIIRDIINEEAADWD(SEQ. ID. No. 27) derived from the sequence of SIV p27. Results are expressed as the highest dilution giving an absorbance $\geq 0.2$.

Western blotting. Serum antibody responses were also assayed by Western blotting using SA I/II, the recombinant polypeptides and a control fraction from *E. coli* BL21 harbouring non-recombinant pET15b. Purified antigens were separated by sodium dodecyl sulphate-polyacrylamide gel electrophoresis (SDS-PAGE) with gels of 10% acrylamide, by using a mini-gel system (Hoeffer Scientific Instruments, San Francisco, Co, USA). Proteins were transferred to nitrocellulose with a semi-dry blotter (Sartorius A. G., Gottingen, Germany). Nitrocellulose strips were blocked with 5% (wt/vol) nonfat milk powder 2.5% (wt/vol) BSA in Tris-HCl-buffered saline (pH 8.0) containing 0.05% (wt/vol) Tween 20. Strips were subsequently incubated with human sera (1 in 20 dilution) or rabbit anti-SA I/II antiserum ($10^{-4}$ dilution) and bound antibody was visualised by using alkaline phosphatase-conjugated secondary antibody with 5-bromo-4-chloro-3-indolylphosphate and nitroblue tetrazolium (Sigma Chemical Co.) as substrates. Each sera was assayed three times and responses were considered as positive if bands were visible in at least two assays.

Bacterial adherence assay. SA I/II mediated adherence of *S. mutans* (Guy's strain) to saliva was assayed by determining binding of [$^3$H]-thymidine labelled bacteria to saliva adsorbed to microtitre wells. Freshly collected human saliva from a single donor was clarified by centrifugation for 10 min at 3000 g, heat-inactivated at 60° C. for 30 min and finally clarified by centrifugation at 17,000 g for 20 min. Treated saliva was diluted with an equal volume of PBS and adsorbed to the wells of a polystyrene 96-well flat-bottomed microtitre plate (Immulon 4; Dynatech) for 2 h at room temperature. After coating, wells were washed three times with PBS and unbound sites were blocked by incubation with 1.5% (wt/vol) BSA in PBS for 1 h at room temperature. Plates were then washed three times with 50 mM KCl-1 mM CaCl$_2$-38 mM MgCl$_2$-1 mM KH$_2$PO$_4$-1.2 mM K$_2$PO$_4$ (pH 7.2; adherence buffer). *S. mutans* cells from an overnight culture in Todd-Hewitt broth were used to inoculate (1/10 volume) a further culture in Todd-Hewitt broth containing 100 µCi (3.7 MBq) [$^3$H]-thymidine (Amersham International plc) per ml. Cells were harvested in late log phase (O.D. 700 nm approximately 0.4) pelleted by centrifugation at 100 g for 10 min and washed three times in adherence buffer. The final suspension was vortexed with 0.5 volume glass beads to break up chains of cocci which was monitored microscopically (Munro et al (1993): Infect. Immun. 61, 4590). Cells were resuspended to $5 \times 10^4$ c.p.m. per 50 µl and BSA was added to 1.5% (wt/vol). Specific activity of the washed *S. mutans* cells was estimated to be $1.3 \times 10^{-3}$ c.p.m. per cell (Munro et al (1985): Infect. Immun. 61, 4590). In competitive inhibition of adherence, the various synthetic peptides were added to the wells (at final concentrations 62.5–500 µM) in 50 µl adherence buffer containing 1.5% (wt/vol) BSA together with 50 µl radiolabelled *S. mutans* suspension. Microtitre plates were incubated at 37° C. for 2 h with gentle shaking and subsequently were washed ten times with adherence buffer. Bound *S. mutans* cells were eluted with 1% (wt/vol) SDS and transferred to glass fibre filters by using the Micromate 196 cell harvester (Canberra Packard, Berks, UK). Filters were counted using the Matrix 96 direct beta counter (Canberra Packard). Background binding was determined on wells to which no saliva was adsorbed. The percentage of binding of *S. mutans* to saliva was calculated by the formula [(test c.p.m.)−(control c.p.m.)/total c.p.m.]×100. Percent inhibition of adherence was calculated as [(percent adherence without inhibitor-percent adherence with inhibitor)/percent adherence without inhibitor]×100. For proteins, determinations of streptococcal adhesion were made in triplicate or quadruplicate at each protein concentration while for peptides, duplicate determinations were made. In each case the assay was performed at least three times.

Statistics

The student's t test was used to analyse results.

Example 1

Preparation of a Panel of Overlapping Synthetic Peptides and Analysis of Their Properties.

T Cell Epitope Mapping

Figure 1:
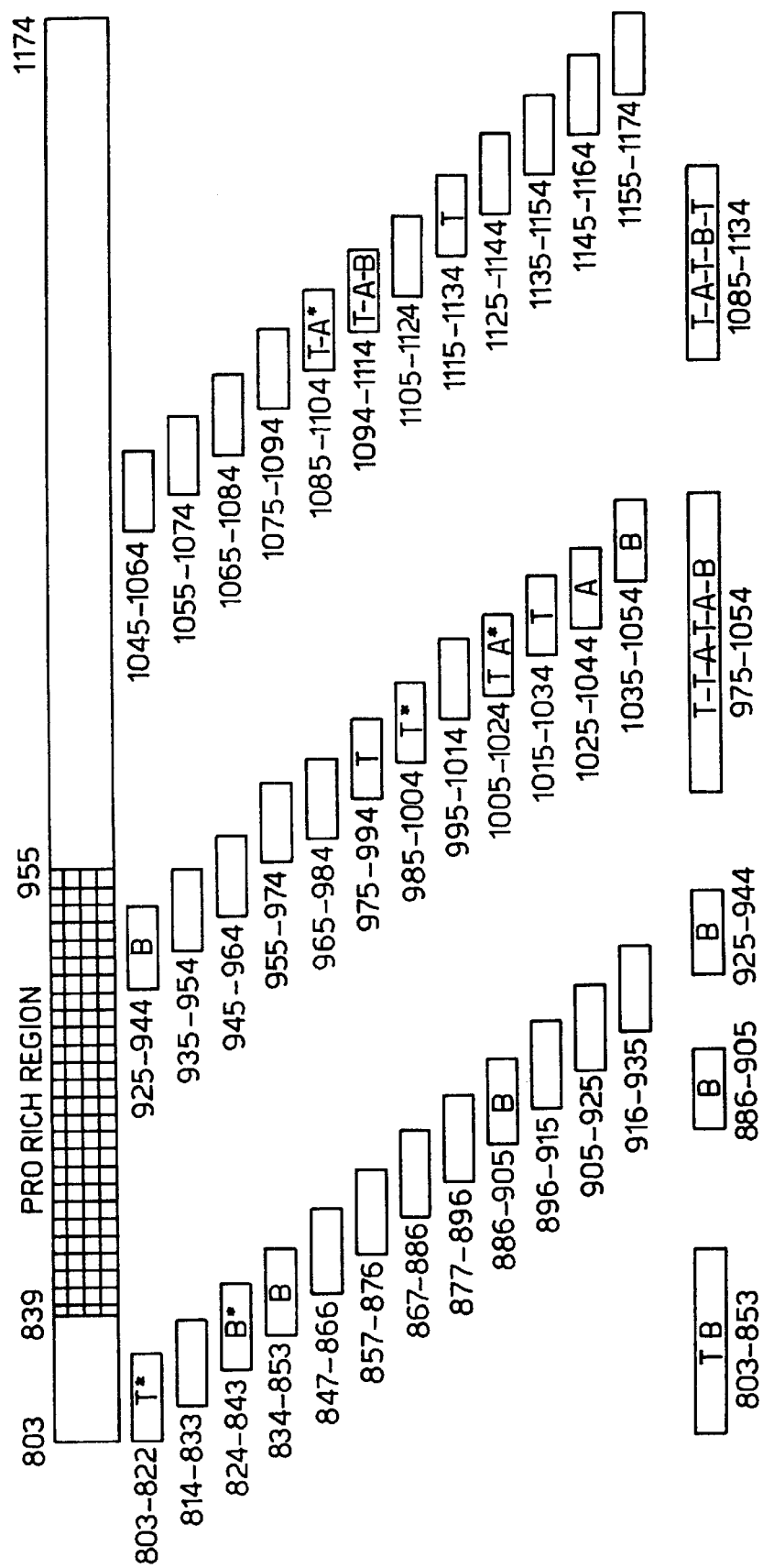
FIG. 1. Depiction of the panel of overlapping 20 mers used to map T-cell, B-cell and adhesion epitopes within SA I/II.

A panel of 32 overlapping synthetic peptides, spanning residues 803–1174 of SA I/II, was prepared, as described above (See FIG. 1). Proliferative responses of PBMCs from 30 subjects were determined by stimulation with peptides (see FIG. 2). All subjects responded to at least one peptide with a band range of 1–8 peptides, and a mean of 4.4 peptides. On the basis of frequency of response to each peptide (SI$\geq$3.0 c.p.m. >500) 3 immunodominant epitopes were identified; peptides 803–822, 975–994 and 985–1004, each yielding frequencies >50% (FIG. 1). Since most (13/15) subjects who responded to peptide 975–994 also responded to peptide 985–1004, it is probable that a single T-cell epitope is present within residues 975–1004. Minor T cell epitopes were also identified within peptides 1005–1024, 1015–1034, 1085–1104 and 1115–1134 with frequencies >20% and some of the adjacent peptides may represent single T cell epitopes.

MHC Restriction of the Lymphoproliferative Responses (See FIG. 3 and Table 2)

HLA restriction of the T cell response was first studied by dose-dependant inhibition with MAb to HLA class I and II antigen (FIG. 2). The lymphoproliferative response was inhibited by 50% with 1 µg of MAb to HLA class II (L243) and 10µg of the MAb inhibited 100% of the responses (from SI 10.0±3.2 to SI 1.5±0.4). Neither MAb to HLA class I (W6/32) nor the isotype control induced any inhibition of the lymphoproliferative response.

The HLA-DR of 17 subjects were determined and 6 of these were homozygous. The responses of the immunodominant and minor epitopes were then studied in the 6 DR homologous subjects (Table 2). Only peptide 975–994 appeared to be restricted by HLA-DR1. The other 6 peptides stimulated lymphocytes from HLA-DR1, 2 (except AA 1085–1104) and DR6 (except AA 803–822). DR5 was restricted by peptide 803–922, though the latter stimulated lymphocytes with DR1, 2 and 3 antigens. Lymphocytes with DR3 or 4 antigen responded to 3 or 4 peptides. The results suggest that except for peptide 975–994, the remaining 6 peptides appear to be promiscuous as they stimulated lymphocytes with 3 to 5 HLA-DR antigens.

TABLE 1

| DR | 803–822 | 975–994 | 985–1004 | 1005–1024 | 1014–1034 | 1085–1104 | 1115–1134 |
|---|---|---|---|---|---|---|---|
| 1 | 4.1 ± 1.0 | 4.0 ± 1.3 | 5.8 ± 1.8 | 3.2 ± 0.6 | 3.3 ± 1.1 | 3.3 ± 1.3 | 3.2 ± 0.6 |
| 2 | 19.3 ± 6.6 | 2.2 ± 0.4 | 16.7 ± 1.7 | 14.6 ± 5.7 | 11.2 ± 5.2 | 0.6 ± 0.3 | 14.7 ± 3.3 |
| 3 | 6.1 ± 2.7 | 0.7 ± 0.2 | 4.1 ± 2.3 | 1.0 ± 0.2 | 2.1 ± 1.7 | 4.3 ± 1.2 | 1.9 ± 2.3 |
| 4 | 2.5 ± 0.8 | 1.8 ± 0.7 | 3.0 ± 0.3 | 3.2 ± 0.5 | 1.6 ± 0.1 | 3.7 ± 0.6 | 1.5 ± 0.7 |
| 5 | 6.8 ± 1.0 | 1.8 ± 1.3 | 2.0 ± 0.8 | 2.3 ± 0.5 | 1.3 ± 0.3 | 1.2 ± 0.4 | 2.9 ± 2.8 |
| 6 | 2.6 ± 1.5 | 2.9 ± 0.9 | 3.5 ± 0.5 | 8.3 ± 3.1 | 5.7 ± 2.4 | 5.6 ± 1.4 | 5.0 ± 2.0 |

The relationship between HLA-DR1-6 and the T cell responses to 7 synthetic peptides.
S.I (± sem) values of subjects homozygous for DR are shown.
Positive responses (S.I. > 3.0, c.p.m. > 500) are in bold.

B Cell Epitope Mapping (see FIG. 4)

Recognition of the recombinant fragments was assessed by Western blotting. Representative blots obtained with sera from 3 individuals are shown in FIG. 3 together with a positive control using rabbit anti-SA I/II antiserum. In panel a, SA I/II, and 984–1161 were recognised strongly. Rabbit anti-SA I/II antiserum used as a positive control (panel d) recognised recombinant 984–1161. The recombinant polypeptide corresponding to residues 984–1161 was also analysed. SA I/II was recognised by all subjects. B cell epitopes were mapped by ELISA using the panel of synthetic peptides. The panel of peptides was screened with sera from 22 individuals and 8 peptides which were recognised by more than one individual, together with one peptide which was not recognised, were selected for further analyses (FIG. 5). SA I/II was recognised by all subjects with mean $\log_2$ titre of 7.6±1.2. Titres against peptides were lower, with only that against peptide 824–843 (mean $\log_2$ titre 4.7±1.1) being significantly greater than the titre against the control SIV p27 peptide (t=7.28 p<0.01). The proportion of significant titres (>mean +2 standard derivations) was also calculated (FIG. 5) and only peptide 824–843 showed high frequency (18/22). Indeed, an immunodominant B cell epitope is present within peptide 824–843, possibly shared with the overlapping peptide 834–853, while peptides 925–944, 1035–1054 and 1085–1104 constitute minor B cell epitopes. Despite the high frequency of responses to the recombinant polypeptide 984–1161 described above, a very low frequency of responses was observed to peptides within this region.

Saliva samples from the subjects were cultured to determine levels of S. mutans. In 66% of individuals S. mutans was detected (range $10^3$–$10^5$ colony forming units/ml). There was no correlation between S. mutans levels and recognition of particular epitopes or titre against SA I/II.

Adhesion Epitope Mapping

Adherence of S. mutans to saliva-coated microtitre wells (a model of the tooth surface) was determined with [$^3$H]-thymidine labelled S. mutans. The proportion of adhering bacteria was in the range 1–5%. In the absence cf saliva, the proportion of adhering bacteria was <0.1%.

In a series of competitive inhibition assays, the panel of synthetic peptides was assayed for inhibition of adhesion of S. mutans to saliva-coated microtitre wells. Peptides 1005–1024, 1025–1044 and 1085–1104 consistently inhibited adhesion with maximal inhibition ≧90% at concentrations of 500 μM (FIG. 6). Adjacent peptides 1015–1034 and 1095–1114 showed more variable and lower inhibition, and may be part of the adhesion epitopes.

Example 2
Construction of the Expression Vector and Expression of a Recombinant Polypeptide of the Invention (SEQ. ID. No. 8).

Using the oligonucleotide primers TAT CAT ATG CAA GAT CTT CCA ACA CCT CCA TCT ATA (5') (SEQ. ID. No. 28) and GTC GAC TCA TAC CAA GAC AAA GGA AGT TGT (3') (SEQ.ID. No. 29) the portion of the SA I/II gene encoding residues 975–1044 (SEQ.ID. No. 8) was amplified by polymerase chain reaction. The amplified gene fragment (with introduced Nde I and Sal I restriction enzyme sites) was cloned using the Ta cloning system and was subcloned into the plasmid pET15b. The recombinant polypeptide was expressed in E. Coli BL21 (DE3).

Example 3
Stimulation of an in vitro T-cell Response by the Recombinant Polypeptide (SEQ. ID. No. 8).

Peripheral blood lymphocytes from human volunteers were prepared as described above. Cells were incubated with purified recombinant polypeptide 975–1044 at concentrations of 40, 10 and 1 μg/ml. Cells were also incuabted with a protein fraction prepared in the same way from E. coli harbouring non-recombinant plasmid. Proliferative responses of 17 subjects were determined. Mean stimulation index (±sem) was 11.6±2.3 compared with 2.4±0.3 for the control. The frequency of subjects responding (i.e. those with stimulation index≧control+2SD) was 15/17.

Example 4
Immunisation of Mice with the Recombinant Polypeptide (SEQ. ID. NO. 8) (See FIG. 7)
i) Groups of mice (3–4 per group) were immunised with 975–1044 (SEQ. ID. No. 8) by two routes:
  a) intraperitoneally with 50 μg polypeptide in incomplete Freund's adjuvant with a boost after 4 weeks (also 50 μg in incomplete Freund's adjuvant and intraperitoneally).
  b) subcutaneously. A single immunisation with 50 μg polypeptide in incomplete Freund's adjuvant.
ii) Draining lymph nodes were removed 10 to 14 days after immunisation, pooled and homogenised to give a single cell suspension in RPMI 1640 culture medium supplemented with 2 mM glutamine, 1 mM pyruvate, 50 mM 2-mercaptoethanol, 100 u/ml penicillin, 100 μg/ml streptomycin, 100 mM HEPES and 5% foetal calf serum. Cells ($2\times10^5$/well) were cultured with antigen and proliferation was measured by incorporation of [$^3$H]-thymidine as described above. Antigens were SA I/II recombinant polypeptides, peptides spanning residues 975–1044 and a control protein fraction from E. coli harbouring non-recombinant plasmid.

As in FIG. 7, all mouse strains responded to SA I/II and the recombinant polypeptide 975–1044 (SEQ. ID. No. 8). Positive responses to peptides were those of stimulation index ≧3.0 (cpm>500). SJL mice responded to peptide 985–1004 and DBA/a mice responded to peptide 975–995 and 985–1004. For BALB/c mice, no significant responses to peptides were observed although the response to peptide 985–1004 was greater than responses to the remaining peptides.

iii) Antibody Recognition (See Table 2)

Sera from mice immunised intraperitoneally with polypeptide 975–1044 recognised intact cells of *S.mutans*, intact SA I/II and recombinant 975–1044. Peptides 995–1014 and 1025–1044 were also recognised. The titre for each strain was as in Table 2, which shows $\log_2$ titres where initial dilution was 1 in 50 (titre=1).

TABLE 2

Antibody recognition of *S. mutans*, SA I/II and peptides.

| STRAIN | ANTIGEN | | | | PEPTIDES | | | | | |
| --- | --- | --- | --- | --- | --- | --- | --- | --- | --- | --- |
| | *S. mutans* | SA I/II | 975–1044 | NR Control | 975–994 | 985–1004 | 995–1014 | 995–1014 | 1015–1034 | 1025–1044 |
| SJL | 4.0 | 4.0 | 10.3 | — | — | — | 8.7 | 1.0 | — | 5.7 |
| DBA/1 | 3.0 | 2.7 | 10.7 | — | 0.7 | 0.7 | 4.7 | 2.0 | — | 7.3 |
| BALB/C | 2.0 | 2.8 | 10.7 | — | — | — | 5.7 | 3.0 | — | 4.7 |

Numbers in the table are $\log_2$ titres (1 = 1:50)

Example 5
Analysis of the Interaction Between Streptococcal Antigen I/II and Salivary Receptor Using BIAcore
AIMS In this study, we have used surface plasmon resonance (spr) to analyse the interaction between purified SA I/II and whole human saliva or purified salivary receptor. In addition we have investigated the calcium dependence of binding, identified individual amino acid residues which may be involved in binding and determined the affinity of the interaction between SA I/II and salivary receptor.
METHODS
Materials SA I/II and recombinant polypeptides were prepared as described above. Salivary receptor was prepared by absorption of whole saliva with intact cells of *S. mutans* (Lee et al (1989) Infect. Immun. 57:3306–3313). The cells were washed with KPBS (2.7 mM KCl, 137 mM NaCl in 1.5 mM $KH_2PO_4$, 6.5 mM $Na_2HPO_4$, pH 7.2)and adsorbed material was eluted with 1 mM EDTA in KPBS. Analysis of the purified material by polyacrylamide gel electrophoresis in the presence of Na dodecyl sulphate indicated the presence of components of Mr>200,000 and approximately 40,000. Peptides were prepared by the simultaneous multiple peptide synthesis procedure (Houghten (1985) Proc. Natl. Acad. Sci. USA 82: 5131–5135) as above. In addition, a series of peptides was synthesised corresponding to residues 1025–1044 in which each residue in turn was substituted by alanine.
Binding Analyses Purified SA I/II or salivary receptor was immobilised on the sensor chip surface at a concentration of 100 $\mu$g/ml in 10 mM Na formate pH 3.5 using the amine coupling kit (Pharmacia Biosensor).
i. Inhibition studies Binding of immobilised SA I/II to receptors in whole saliva was determined in the absence and presence of inhibitors (at varying concentrations). Inhibition by alanine-substituted peptides was analysed at a peptide concentration of 50 $\mu$M. The running buffer was HEPES buffered saline (HBS) and the surface was regenerated with 100 mM HCl.
ii. Direct Binding Purified salivary receptor was immobilised on the sensor chip and binding of SA I/II or purified recombinant polypeptide fragments was determined.

RESULTS
i. Calcium Dependency

In separate determinations with whole saliva, binding to immobilised SA I/II varied from approximately 250 resonance units (RU)—800 RU. In the presence of EDTA, binding was inhibited with maximal inhibition of 95% at a concentration of 10 mM EDTA. Subsequent binding assays were performed in the presence of 5 mM calcium.
ii. Inhibition of Binding Purified SA I/II or recombinant polypeptide fragments 1 (residues 39–481), 2 (residues 475–824), 3 (residues 816–1213), 4 (residues 1155–1538) and recombinant 984–1161 were added to fluid phase saliva as competitive inhibitors at concentrations varying from 0–20 $\mu$M. SA I/II inhibited binding most efficiently with approximately 90% inhibition at a concentration of 6 $\mu$M (FIG. 8). Of the recombinant fragments, only fragment 3 and r984–1161 inhibited binding to salivary receptors to a significantly greater extent than the control (bovine serum albumin) with maximal inhibition of 65% and 50%, respectively (FIG. 8).

A panel of synthetic peptides (20mers overlapping by 10) spanning residues 803–1174 was assayed for inhibitory activity. Peptide 1025–1044 was the most effective inhibitor although 10–20 fold higher concentrations were required than for polypeptides (FIG. 9). A panel of peptides in which each of the residues 1025–1044 in turn were substituted with alanine (alanine was substituted by serine where it occurred naturally) was also analysed for inhibitory activity. Substitution of Glu (1037) consistently abolished inhibition mediated by the peptide (FIG. 10). Similarly, substition of Gln 1025, Thr 1039, Phe 1041, Val 1042, Leu 1043 and Val 1044 reduced the inhibition of binding which was mediated by the peptide 1025–1044.
iii. Direct Binding For these analyses, purified salivary receptor was immobilised on the sensor chip and binding to fluid phase SA I/II or recombinant polypeptides was determined. At a concentration of approximately 5 $\mu$M both SA I/II and recombinant SA I/II bound to salivary receptor in the range 500–600 RU (FIG. 11). Binding of recombinant polypeptides was determined at a concentration of approximately 20$\mu$M and highest binding was obtained with fragment 3 (1256 RU) (FIG. 11). Binding of other fragments although significantly greater than the myosin control was not greater than the bovine serum albumin control and thus does not appear to be specific. Addition of EDTA (10 $\mu$M) in this assay completely inhibited binding of fluid phase SA I/II.

Affinity and rate constants for the adhesir-receptor interaction were determined for SA I/II, recombinant SA I/II and fragment 3 (Table 3). The values indicate a low affinity interaction with a slow association rate constant and a relatively rapid- dissociation constant.
Conclusions These analyses confirm that residues 816–1213 of SA I/II form an adhesion binding region and that within this region, peptide 1025–1044 forms an adhesion epitope. We have now extended these findings by identifying specific residues which may be essential for binding to salivary receptor, namely residues 1025, 1037, 1039 and 1041–1045. The binding is EDTA sensitive and, under the assay conditions, is of relatively low affinity.

TABLE 3

| | | SA I/II | recomb. SA I/II | FRAG 3 |
|---|---|---|---|---|
| $k_a$ | $(M^{-1} s^{-1})$ | n.d. | $20.9 \times 10^3$ | $1.5 \times 10^3$ |
| $k_d$ | $(s^{-1})$ | $2 \times 10^{-2}$ | $4.2 \times 10^{-3}$ | $8.1 \times 10^{-3}$ |
| $K_A$ | $(M^{-1})$ | n.d. | $5.0 \times 10^6$ | $0.2 \times 10^6$ | n.d. not determined

SEQUENCE INFORMATION

As a result of the experiments detailed above, the following sequences have been identified as being of particular interest.

(i) Residues 925 to 1114 (SEQ. ID. No. 1). This sequence comprises sequences (iv) and (v) below and includes 2 series of overlapping T-cell, B-cell and adhesion epitopes, a further B-cell epitope, a further T-cell epitope and an adhesion site.
SEQ. ID. No. 1:
TEKPLEPAPVEPSYEAEPTPPTPTPDQPEPNK-
PVEPTYEVIPTPPTDPVYQDLPTPP-
SIPTVHFHYFKLAVQPQVNKEIRNNND-
VNIDRTLVAKQSVVKFQLKTADLPAGRDETTSEV
LVDPLPSGYQFNPEATKAASPGFDVAYD-
NATNTVTFKATAATLATFNADLTKSVATIYP
TVVGQVLNDGATY Its DNA sequence is (SEQ.ID.No. 12):
ACAGAAAAGCCGTTGGAGCCAGCACCT-
GTTGAGCCAAGCTATGAAGCAGAGCCAACGCCA
CCGACACCAACACCAGATCAACCAGAAC-
CAAACAAACCTGTTGAGCCAACTTATGAGGTT
ATTCCAACACCGCCGACTGATCCTGTT-
TATCAAGATCTTCCAACACCTCCATCTATACCA
ACTGTTCATTTCCATTACTTTAAAC-
TAGCTGTTCAGCCGCAGGTTAACAAA-
GAAATTAGA AACAATAACGATGTTAATATTGACA-
GAACTTTGGTGGCTAAACAATCTGTTGTTAAGTTC
CAGCTGAAGACAGCAGATCTCCCTGCTG-
GACGTGATGAAACAACTTCCTTTGTCTTGGTA
GATCCCCTGCCATCTGGTTATCAATT-
TAATCCTGAAGCTACAAAAGCTGCCAGC-
CCTGGC TTTGATGTCGCTTATGATAATGCAAC-
TAATACAGTCACCTTCAAGGCAACTGCAGCAACT
TTGGCTACGTTTAATGCTGATTTGAC-
TAAGTCAGTGGCAACGATTTATCCAACAGTGGTC
GGACAAGTTCTTAATGATGGCGCAACTTAT (ii) Residues 1005 to 1044 (SEQ. ID. No. 2). This comprises a T-cell epitope overlapping two adhesion sites.
SEQ. ID. No. 2:
NNNDVNIDRTLVAKQSWKFQLK-
TADLPAGRDETTSFVLV Its DNA sequence is (SEQ. ID. No. 13):
AACAATAACGATGTTAATATTGACA-
GAACTTTGGTGGCTAAACAATCTGTTGT-
TAAGTTC CAGCTGAAGACAGCAGATCTCCCT-
GCTGGACGTGATGAAACAACTTCCTTTGTCTTGGTA (iii) Residues 1085–1104 (SEQ. ID. No. 3). Here, a T-cell epitope, a B-cell epitope and an adhesion site overlap.
SEQ. ID. No. 3:
LATFNADLTKSVATIYPTVV Its DNA sequence is (SEQ. ID. No. 14):
TTGGCTACGTTTAATGCTGATTTGAC-
TAAGTCAGTGGCAACGATTTATCCAACAGTGGTC (iv) Residues 1005 to 1114 (SEQ. ID. No. 4). This comprises sequences (ii) and (iii) above and therefore includes two sequences in which a B-cell epitope a T-cell epitopes and an adhesion site overlap.
SEQ. ID. No. 4:
NNNDVNIDRTLVAKQSVVKFQLK-
TADLPAGRDETTSFVLVDPLPSGYQFN-
PEATKAASPGF DVAYDNATNTVTFKATAATLAT-
FNADLTKSVATIYPTVVGQVLNDGATY Its DNA sequence is (SEQ. ID. No. 15):
AACAATAACGATGTTAATATTGACA-
GAACTTTGGTGGCTAAACA ATCTGTTGT-
TAAGTTC CAGCTGAAGACAGCAGATCTCCCT-
GCTGGACGTGATGAAACAACTTCCTTTGTCTTGGTA
GATCCCCTGCCATCTGGTTATCAATT-
TAATCCTGAAGCTACAAAAGCTGCCAGC-
CCTGGC TTTGATGTCGCTTATGATAATGCAAC-
TAATACAGTCACCTTCAAGGCAACTGCAGCAACT
TTGGCTACGTTTAATGCTGATTTGAC-
TAAGTCAGTGGCAACGATTTATCCAACAGTGGTC
GGACAAGTTCTTAATGATGGCGCAACTTAT (v) Residues 925 to 1004 (SEQ. ID. No. 5). This comprises a B-cell epitope, an immunodominant T-cell epitope and an adhesion site.
SEQ. ID. No. 5:
TEKPLEPAPVEPSYEAEPTPPTPTP-
DQPEPNKPVEPTYEVIPTPPTDPVYQDLPTPPSIPT
VHFHYFKLAVQPQVNKEIR Its DNA sequence is (SEQ. ID. No. 16):
ACAGAAAAGCCGTTGGAGCCAGCACCT-
GTTGAGCCAAGCTATGAAGCAGAGCCAACGCCA
CCGACACCAACACCAGATCAACCAGAAC-
CAAACAAACCTGTTGAGCCAACTTATGAGGTT
ATTCCAACACCGCCGACTGATCCTGTT-
TATCAAGATCTTCCAACACCTCCATCTATACCA
ACTGTTCATTTCCATTACTTTAAAC-
TAGCTGTTCAGCCGCAGGTTAACAAA-
GAAATTAGA (vi) Residues 925 to 1054 (SEQ. ID. No. 6). This comprises sequence (v) above, together with a further adjacent adhesion site and a further overlapping B-cell epitope.
SEQ ID. No. 6:
TEKPLEPAPVEPSYEAEPTPPTPTP-
DQPEPNKPVEPTYEVIPTPPTDPVYQDLPTPPSIPT
VHFHYFKLAVQPQVNKEIRNNND-
VNIDRTLVAKQSVVKFQLKTADLPAGR-
DETTSFVLVDP LPSGYQFN Its DNA sequence is (SEQ. ID. No. 17):
ACAGAAAAGCCGTTGGAGCCAGCACCT-
GTTGAGCCAAGCTATGAAGCAGAGCCAACGCCA
CCGACACCAACACCAGATCAACCAGAAC-
CAAACAAACCTGTTGAGCCAACTTATGAGGTT
ATTCCAACACCGCCGACTGATCCTGTT-
TATCAAGATCTTCCAACACCTCCATCTATACCA
ACTGTTCATTTCCATTACTTTAAAC-
TAGCTGTTCAGCCGCAGGTTAACAAA-
GAAATTAGA AACAATAACGATGTTAATATTGACA-
GAACTTTGGTGGCTAAACAATCTGTTGTTAAGTTC
CAGCTGAAGACAGCAGATCTCCCTGCTG-
GACGTGATGAAACAACTTCCTTTGTCTTGGTA
GATCCCCTGCCATCTGGTTATCAATTTAAT (vii) Residues 803–854 (SEQ. ID. No. 7). This comprises a major T-cell epitope and adjacent immunodominant B-cell epitope.

SEQ. ID. No. 7:
ETGKKPNIWYSLNGKIRAVNLPKVTKEKPTPPVKPTAPTKPTYETEKPLKPA
Its DNA sequence is (SEQ. ID. No. 18)
GAAACCGGCAAAAAACCAAATATTTGGTATTCATTAAATGGTAAAATCCGTGCGGTTAATCTTCCTAAAGTTACTAAGGAAAAACCCACACCTCCGGTTAAACCAACAGCTCCAACTAAACCAACTTATGAAACAGAAAAGCCATTAAAACCGGCA (viii) Residues 975 to 1044 (SEQ. ID. No. 8). This comprises a T-cell epitope, a B-cell epitope and an adhesion site.
SEQ. ID No. 8:
QDLPTPPSIPTVFHYFKLAVQPQVNKEIRNNNDVNIDRTLVAKQSVVKFQLKTADLPAGR DETTSFVLV
Its DNA sequence is (SEQ. ID. No. 19):
CAAGATCTTCCAACACCTCCATCTATACCAACTGTTCATTTCCATTACTTTAAACTAGCTGTTCAGCCGCAGGTTAACAAAGAATTAGAAACAATAACGATGTTAATATTGACAGAACTTTGGTGGCTAAACAACTTGTTAAGTTCCAGCTGAAGAAGCAGATCTCCCTGCTGGA CGTGATGAAACAACTTCCTTTGTCTTGGTA (ix) Residues 1024 to 1044 (SEQ. ID. No. 9). This comprises a T-cell epitope overlapping with an adhesion site.
SEQ. ID. No. 9:
FQLKTADLPAGRDETTSFVLV
Its DNA Sequence is (SEQ. ID. No. 20):
TTCCAGCTGAAGACAGCAGATCTCCCTGCTGGACGTGATGAAACAACTTCCTTTGTCTTGGTA (x) Residues 803 to 1114 (SEQ. ID. No. 10). This comprises sequences (i) and (vii) above and some intervening sequence. Residues 803 to 1114 comprise 2 series of overlapping T-cell, B-cell and adhesion epitopes, a further T-cell epitope and a further adhesion site and an immunodominant B-cell epitope and a major T-cell epitope.
SEQ. ID. No. 10:
ETGKKPNIWYSLNGKIRAVNLPKVTKEKPTPPVKPTAPTKPTYETEKPLKPAPV
APNYEKEPTPPTRTPDQAEPKKPTPPTYETEKPLEPAPVEPSYEAEPTPPTRTPDQAE PNKPTPPTYETEKPLEPAPVEPSYEAEPTPPTPTPDQPEPNKPVEPTYEVIPTPPTDP
VYQDLPTPPSIPTVFHYFKLAVQPQVNKEIRNNNDVNIDRTLVAKQSVVKFQLKTAD LPAGRDETTSFVLVDPLSGYQFNPEATKAASPGFDVAYDNATNTVTFKATAAT LATF NADLTKSVATIYPTVVGQVLNDGATY
Its DNA Sequence is (SEQ. ID. NO. 21):
GAAACCGGCAAAAAACCAAATATTTGGTATTCATTAAATGGTAAAATCCGTGCGGTTAATCTTCCTAAAGTTACTAAGGAAAAACCCACACCTCCGGTTAAACCAACAGCTCCAACTAAACCAACTTATGAAACAGAAAAGCCATTAAAACCGGCACCAGTAGCTCCAAATTATGAAAAG GAGCCAACCACCACCGACAAGAACACCGGATCAAGCAGAGCCAAAGAAACCCACTCCGCCG ACCTATGAAACAGAAAAGCCGTTGGAGCCAGCACCTGTTGAGCCAAGCTATGAAGCAGAG CCAACACCGCCGACAAGGACACCGGATCAGGCAGAGCCAAATAAACCCACACCGCCGACC TATGAAACAGAAAAGCCGTTGGAGCCAGCACCTGTTGAGCCAAGCTATGAAGCAGAGCCA ACGCCACCGACACCAACACCAGATCAACCAGAACCAAACAAACCTGTTGAGCCAACT TAT GAGGTTATTCCAACACCGCCGACTGATCCTGTTTATCAAGATCTTCCAACACCTCCATCT ATACCAACTGTTCATTTCCATTACTTTAAACTAGCTGTTCAGCCGCAGGTTAACAAAGAA ATTAGAAACAATAACGATGTTAATATTGACAGAACTTTGGTGGCTAAACAATCTGTTGTT AAGTTCCAGCTGAAGACAGCAGATCTCCCTGCTGGACGTGATGAAACAACTTCCTTTGTC TTGGTAGATCCCCTGCCATCTGGTTATCAATTTAATCCTGAAGCTACAAAAGCTGCCAGC CCTGGCTTTGATGTCGCTTATGATAATGCAACTAATACAGTCACCTTCAAGGCAACGCA GCAACTTTGGCTACGTTTAATGCTGATTTGACTAAGTCAGTGGCAACGATTTATCC I .ACA GTGGTCGGACAAGTTCTTAATGATGGCGCAACTTAT (xi) Residues 975 to 1004 (SEQ. ID. No. 11), which comprise a T-cell epitope.
SEQ. ID. No. 11:
QDLPTPPSI PTVHFHYFKLAVQPQVNKEIR
Its DNA Sequence is (SEQ. ID. NO. 22):
CAAGATCTTCCAACACCTCCATCTATACCAACTGTTCATTTCCATTACTTTAAACTAGCTGTTCAGCCGCAGGTTAACAAAGAAATTAGA The amino acid sequence of SA I/II is as follows, beginning with residue No. 1 (SEQ ID No. 23).
MKVKKTYGFRKSKISKTLCGAVLGTVAAVSVAGQKVFADETTTT SDVDTKVVGTQTGNPATNLPEAQGSASKQAEQSQTKLERQMVHTIEVPKTDLDQAAKD
AKSAGVNVVQDADVNKGTVKTAEEAVQKETEIKEDYTKQAEDIKKTTDQYKSDVAAHE AEVAKIKAKNQATKEQYGKDMVAHKAEVERINAANAASKTAYEAKLAQYQADLAAVQK TNAANQASYQKALAAYQAELKRVQEANAAAKAAYDTAVAANNAKNTEIAAANEEIRKR NATAKAEYETKLAQYQAELKRVQEANAANEADYQAKLTAYQTEL ARVQKANADAKAAY EAAVAANNAKNAALTAENTAIKQRNENAKATYEAALKQYEADLAAVKKANAANEADYQ AKLTAYQTELARVQKAN ADAKANAAVAANNAANAALTAENTAIKKRNADAKADYEA KLAKYQADLAKYQKDLADYPVKLKAYEDEQASIKAALELEKHKNEDGNLTEPSAQNL
VYDLEPNANLSLTTDGKFLKASAVDDAFSKSTSKAKYDQKILQLDDLDITNLEQSNDV ASSMELYGNFGDKAGWSTTVSNNSQVKWGSVLLERGQSATATYTNLQNSYYNGKKISK IVYKYTVDPKSKFQGQKVWLGIFTDPTLGVFASAYTGQVEKNTSIFIKNEFTFYDEDG KPINFDNALLSVASLNRENNSIEMAKDYTGKFVKISGSSIGEKNGMIYATDTLNFRQG QGGARWTMYTRASEPGSGWDSSDAPNSWYGAGAIRMSGPNNSVTLGAISSTLWPADP TMAIETGKKPNIWYSLNGKIRAVNLPKVTKEKPTPPVKPTAPTKPTYETEKPLKPAPV APNYEKEPTPPTRTPDQAEPKKPTPPTYETEKPLEPAPVEPSYEAEPTPPTRTPDQAE PNKPTPPTYETEKPLEPAPVEPSYEAEPTPPTPTPDQPEPNKPVEPTYEVIPTPPTDP VYQDLPTPPSIPTVHFHYFKLAVQPQVNKEIRNNNDVNIDRTLVAKQSVVKFQLKTAD LPAGRDETTSFVLVDPLSGYQFNPEATKAASPGFDVAYDNATNTVTFKATAA TLATE NADLTKSVATIYPTVVGQVLNDGATYKNNFSLTVNDAYGIKSNVVRVTTPGKPNDPDN PNNNYIKPTKVNKENGVVIDGKTVLAG- STNYYELTWDLDQYKNDRSSADTIQQGFYY
VDDYPEEALELRQDLVKITDANGNEVT-
GVSVDNYTSLEAAPQEIRDVLSKAGIRPKGA FQI-
FRADNPREFYDTYVKTGIDLKIVSPMV-
VKKQMGQTGGSYEDQAYQIDFGNGYASN
IVINNVPKINPKKDVTLTLDPADT-
NNVDGQTIPLNNYRLIGGIIPANHSEELFEY NFYD-
DYDQTGDHYTGQYKVFAKVDITLKNGVI-
IKSGTELTQYTTAEVDTTKGAITIKF
KEAFLRSVSIDSAFQAESYIQMKRIA-
VGTFENTYINTVNGVTYSSNTVKTTTPEDPAD
PTDPQDPSSPRTSTVIIYK-
PQSTAYQPSSVQKTLPNTGVTNNAYM-
PLLGIIGLVTSFSL LGLKAKKD Its DNA sequence is as follows (SEQ ID No. 24):

1 ATTTCAGCAA AAATTGACAA ATCAAATCAA TTATATTACA ATTTTTAAC
51 GTATATTACA AAAATATATT TGGAAGATTT ATTCAGATTT GGAGGATTTA
101 TGAAAGTCAA AAAAACTTAC GGTTTTCGTA AAAGTAAAAT TAGTAAAACA
151 CTGTGTGGTG CTGTTCTAGG AACAGTAGCA GCAGTCTCTG TAGCAGGACA
201 AAAGGTTTTT GCCGATGAAA CGACCACTAC TAGTGATGTA GATACTAAAG
251 TAGTTGGAAC ACAAACTGGA AATCCAGCGA CCAATTTGCC AGAGGCTCAA
301 GGAAGTGCGA GTAAGCAAGC TGAACAAAGT CAAACCAAGC TGGAGAGACA
351 AATGGTTCAT ACCATTGAAG TACCTAAAAC TGATCTTGAT CAAGCAGCAA
401 AAGATGCTAA GTCTGCTGGT GTCAATGTTG TCCAAGATGC CGATGTTAAT
451 AAAGGAACTG TTAAAACAGC TGAAGAAGCA GTCCAAAAAG AAACTGAAAT
501 TAAAGAAGAT TACACAAAAC AAGCTGAGGA TATTAAGAAG ACAACAGATC
551 AATATAAATC GGATGTAGCT GCTCATGAGG CAGAAGTTGC TAAAATCAAA
601 GCTAAAAATC AGGCAACTAA AGAACAGTAT GGAAAAGATA TGGTAGCTCA
651 TAAAGCCGAG GTTAACGCA TTAATGCTGC AAATGCTGCC AGTAAAACAG
701 CTTATGAAGC TAAATTGGCT CAATATCAAG CAGATTTAGC AGCCGTTCAA
751 AAAACCAATG CTGCCAATCA AGCATCCTAT CAAAAAGCCC TTGCTGCTTA
801 TCAGGCTGAA CTGAAACGTG TTCAGGAAGC TAATGCAGCC GCCAAAGCCG
851 CTTATGATAC TGCTGTAGCA GCAAATAATG CCAAAAATAC AGAAATTGCC
901 GCTGCCAATG AAGAAATTAG AAAACGCAAT GCAACGGCCA AGCTGAATA
951 TGAGACTAAG TTAGCTCAAT ATCAAGCTGA ACTAAAGCGT GTTCAGGAAG
1001 CTAATGCCGC AAACGAAGCA GACTATCAAG CTAAATTGAC CGCCTATCAA
1051 ACAGAGCTTG CTCGCGTTCA GAAAGCCAAT GCAGATGCTA AAGCGGCCTA
1101 TGAAGCAGCT GTAGCAGCAA ATAATGCCAA AAATGCGGCA CTTACAGCTG
1151 AAAATACTGC AATTAAGCAA CGCAATGAGA ATGCTAAGGC GACTTATGAA
1201 GCTGCACTCA AGCAATATGA GGCTGATTTG GCAGCGGTGA AAAAAGCTAA
1251 TGCCGCAAAC GAAGCAGACT ATCAAGCTAA ATTGACCGCC TATCAAACAG
1301 AGCTCGCTCG CGTTCAAAAG GCCAATGCGG ATGCTAAAGC GGCCTATGAA
1351 GCAGCTGTAG CAGCAAATAA TGCCGCAAAT GCAGCGCTCA CAGCTGAAAA
1401 TACTGCAATT AAGAAGCGCA ATGCGGATGC TAAAGCTGAT TACGAAGCAA
1451 AACTTGCTAA GTATCAAGCA GATCTTGCCA AATATCAAAA AGATTTAGCA
1501 GACTATCCAG TTAAGTTAAA GGCATACGAA GATGAACAAG CTTCTATTAA
1551 AGCTGCACTG GCAGAACTTG AAAAACATAA AAATGAAGAC GGAAACTTAA
1601 CAGAACCATC TGCTCAAAAT TTGGTCTATG ATCTTGAGCC AAATGCGAAC
1651 TTATCTTTGA CAACAGATGG GAAGTTCCTT AAGGCTTCTG CTGTGGATGA
1701 TGCTTTTAGC AAAAGCACTT CAAAAGCAAA ATATGACCAA AAAATTCTTC
1751 AATTAGATGA TCTAGATATC ACTAACTTAG AACAATCTAA TGATGTTGCT
1801 TCTTCTATGG AGCTTTATGG CAATTTTGGT GATAAAGCTG GCTGGTCAAC
1851 GACAGTAAGC AATAACTCAC AGGTTAAATG GGGATCGGTA CTTTTAGAGC
1901 GCGGTCAAAG CGCAACAGCT ACATACACTA ACCTGCAGAA TTCTTATTAC
2001 GTCCAAGTTT CAAGGTCAAA AGGTTTGGTT AGGTATTTTT ACCGATCCAA
1951 AATGGTAAAA AGATTTCTAA AATTGTCTAC AAGTATACAG TGGACCCTAA
2051 CTTTAGGTGT TTTTGCTTCC GCTTATACAG GTCAAGTTGA AAAAAACACT
2101 TCTATTTTTA TTAAAAATGA ATTCACTTTC TATGACGAAG ATGGAAAACC
2151 AATTAATTTT GATAATGCCC TTCTATCAGT AGCTTCTCTT AACCGAGAAA
2201 ATAATTCTAT TGAGATGGCC AAAGATTATA CGGGTAAATT TGTCAAAATC
2251 TCTGGATCAT CTATCGGTGA AAAGAATGGC ATGATTTATG CTACAGATAC
2301 TCTCAACTTT AGGCAGGGTC AAGGTGGTGC TCGTTGGACC ATGTATACCA
2351 GAGCTAGCGA ACCGGGATCT GGCTGGGATA GTTCAGATGC GCCTAACTCT
2401 TGGTATGGTG CTGGTGCTAT CCGCATGTCT GGTCCTAATA ACAGTGTGAC
2451 TTTGGGTGCT ATCTCATCAA CACTTGTTGT GCCTGCTGAT CCTACAATGG
2501 CAATTGAAAC CGGCAAAAAA CCAAATATTT GGTATTCATT AAATGGTAAA
2551 ATCCGTGCGG TTAATCTTCC TAAAGTTACT AAGGAAAAAC CCACACCTCC
2601 GGTTAAACCA ACAGCTCCAA CTAAACCAAC TTATGAAACA GAAAAGCCAT
2651 TAAAACCGGC ACCAGTAGCT CCAAATTATG AAAAGGAGCC AACACCACCG
2701 ACAAGAACAC CGGATCAAGC AGAGCCAAAG AAACCCACTC CGCCGACCTA

2751 TGAAACAGAA AAGCCGTTGG AGCCAG-
CACC TGTTGAGCCA AGCTATGAAG
2801 CAGAGCCAAC ACCGCCGACA AGGACAC-
CGG ATCAGGCAGA GCCAAATAAA
2851 CCCACACCGC CGACCTATGA AACA-
GAAAAG CCGTTGGAGC CAGCACCTGT
2901 TGAGCCAAGC TATGAAGCAG AGC-
CAACGCC ACCGACACCA ACACCAGATC
2951 AACCAGAACC AAACAAACCT GTTGAGC-
CAA CTTATGAGGT TATTCCAACA
3001 CCGCCGACTG ATCCTGTTTA TCAAGATCTT
CCAACACCTC CATCTATACC
3051 AACTGTTCAT TTCCATTACT TTAAACTAGC
TGTTCAGCCG CAGGTTAACA
3101 AAGAAATTAG AAACAATAAC GATGTTAATA
TTGACAGAAC TTTGGTGGCT
3151 AAACAATCTG TTGTTAAGTT CCAGCTGAAG
ACAGCAGATC TCCCTGCTGG
3201 ACGTGATGAA CAACTTCCT TTGTCTTGGT
AGATCCCCTG CCATCTGGTT
3251 ATCAATTTAA TCCTGAAGCT ACAAAAGCTG
CCAGCCCTGG CTTTGATGTC
3301 GCTTATGATA ATGCAACTAA TACAGTCACC
TTCAAGGCAA CTGCAGCAAC
3351 TTTGGCTACG TTTAATGCTG ATTTGACTAA
GTCAGTGGCA ACGATTTATC
3401 CAACAGTGGT CGGACAAGTT CTTAATGATG
GCGCAACTTA TAAGAATAAT
3451 TTCTCGCTCA CAGTCAATGA TGCTTATGGC
ATTAAATCCA ATGTTGTTCG
3501 GGTGACAACT CCTGGTAAAC CAAATGATCC
AGATAACCCA AATAATAATT
3551 ACATTAAGCC AACTAAGGTT AATAAAAATG
AAAATGGCGT TGTTATTGAT
3601 GGAAAACAG TTCTTGCCGG TTCAACGAAT
TATTATGAGC TAACTTGGGA
3651 TTGGATCAA TATAAAAACG ACCGCTCTTC
AGCAGATACC ATTCAACAAG
3701 GATTTTACTA TGTAGATGAT TATCCAGAAG
AAGCGCTTGA ATTGCGTCAG
3751 GATTTAGTGA AGATTACAGA TGCTAATGGC
AATGAAGTTA CTGGTGTTAG

3801 TGTGGATAAT TATACTAGTC TTGAAGCAGC
CCCTCAAGAA ATTAGAGATG
3851 TTCTTTCTAA GGCAGGAATT AGACCTAAAG
GTGCTTTCCA AATTTTCCGT
3901 GCCGATAATC CAAGAGAATT TTATGATACT
TATGTCAAAA CTGGAATTGA
3951 TTTGAAGATT GTATCACCAA TGGTTGTTAA
AAAACAAATG GGACAAACAG
4001 GCGGGAGTTA TGAAGATCAA GCTTACCAAA
TTGACTTTGG TAATGGTTAT
4051 GCATCAAATA TCGTTATCAA TAATGTTCCT
AAGATTAACC CTAAGAAAGA
4101 GTGACCTTA ACACTTGATC CGGCTGATAC
AAATAATGTT GATGGTCAGA
4151 CTATTCCACT TAATACAGTC TTTAATTACC
GTTTGATTGG TGGCATTATC
4201 CCTGCAAATC ACTCAGAAGA ACTCTTTGAA
TACAATTTCT ATGATGATTA
4251 TGATCAAACA GGAGATCACT ATACTGGTCA
GTATAAAGTT TTTGCCAAGG
4301 TTGATATCAC TCTTAAAAAC GGTGTTATTA
TCAAGTCAGG TACTGAGTTA
4351 ACTCAGTATA CGACAGCGGA AGTTGATACC
ACTAAAGGTG CTATCACAAT
4401 TAAGTTCAAG GAAGCCTTTC TGCGTTCTGT
TTCAATTGAT TCAGCCTTCC
4451 AAGCTGAAAG TTATATCCAA ATGAAACGTA
TTGCGGTTGG TACTTTTGAA
4501 AATACCTATA TTAATACTGT CAATGGGGTA
ACTTACAGTT CAAATACAGT
4551 GAAAACAACT ACTCCTGAGG ATCCTGCAGA
CCCTACTGAT CCGCAAGATC
4601 CATCATCACC GCGGACTTCA ACTGTAATTA
TCTACAAACC TCAATCAACT
4651 GCTTATCAAC CAAGCTCTGT CCA AAAACG
TTACCAAATA CGGGAGTAAC
4701 AAACAATGCT TATATGCCTT TACTTGGTAT
TATTGGCTTA GTTACTAGTT
4751 TTAGTTTGCT TGGCTTAAAG GCTAAGAAAG
ATTGACAGCA TAGATATTAC
4801 ATTAGAATTA AAAAGTGAGA TGAAGCGATA
AATCACAGAT TGAGCTTTTA
4851 TCTCATTTTT TGATT

---

What is claimed is:

1. A polypeptide selected from the group consisting of:
  a) a first polypeptide consisting of
    i) a sequence of no more than 100 consecutive amino acids of SAI/II (SEQ. ID. NO: 23) which said sequence comprises the amino acid sequence of residues 1025–1044 of SAI/II (residues 2–21 of SEQ ID NO: 9) or residues 1024–1044 (SEQ. ID. NO: 9); or
    ii) modified amino acid sequence which differs from the sequence of i) by up to and including 8 amino acid alterations wherein said alterations consist of the substitution and/or deletion and/or insertion of up to and including 8 amino acids wherein the polypeptide containing said modified amino acid sequence has the same immunological and adhesion properties as the polypeptide of i); and b) a second polypeptide which is an extended form of said first polypeptide of i) or ii), which second polypeptide comprises said first polypeptide extended at the N-terminus or the C-terminus of said first polypeptide, or both, with non-wild-type amino acid sequence to form said second polypeptide; wherein non-wildtype amino acid sequence is defined as an amino acid sequence which does not natively occur at the N-terminus or C-terminus of said first polypeptide in SAI/II (SEQ. ID. NO: 23); and wherein said first polypeptide or second polypeptide may be in the N-terminal acylated and/or C-terminal amidated form.

2. A first polypeptide or a second polypeptide according to claim 1 wherein said first polypeptide is no more than 50 amino acids in length.

3. A first polypeptide or second polypeptide according to claim 1 wherein said first polypeptide is from 20 to 50 amino acids in length.

4. A first polypeptide or second polypeptide according to claim 1 wherein said first polypeptide is from 50 to 100 amino acids in length.

5. The first polypeptide or second polypeptide of claim 1 wherein the first polypeptide consists of 20–100 consecutive amino acids of SAI/II (SEQ. ID. NO: 23).

6. A pharmaceutical composition comprising the first polypeptide or second polypeptide of claim 1 in a pharmaceutically acceptable carrier.

7. A pharmaceutical composition comprising the first polypeptide or second polypeptide of claim 2 in a pharmaceutically acceptable carrier.

8. A pharmaceutical composition comprising the first polypeptide or second polypeptide of claim 3 in a pharmaceutically acceptable carrier.

9. A pharmaceutical composition comprising the first polypeptide or second polypeptide of claim 4 in a pharmaceutically acceptable carrier.

10. A pharmaceutical composition comprising the first polypeptide or second polypeptide of claim 5 in a pharmaceutically acceptable carrier.

11. The composition of claim 6 which is formulated for topical application in the mouth.

12. The composition of claim 7 which is formulated for topical application in the mouth.

13. The composition of claim 8 which is formulated for topical application in the mouth.

14. The composition of claim 9 which is formulated for topical application in the mouth.

15. The composition of claim 10 which is formulated for topical application in the mouth.

16. A method to vaccinate or treat a mammalian host against dental caries which method comprises administering to said host an effective amount of the first polypeptide or second polypeptide of claim 1.

17. A method to vaccinate or treat a mammalian host against dental caries which method comprises administering to said host an effective amount of the first polypeptide or second polypeptide of claim 2.

18. A method to vaccinate or treat a mammalian host against dental caries which method comprises administering to said host an effective amount of the first polypeptide or second polypeptide of claim 3.

19. A method to vaccinate or treat a mammalian host against dental caries which method comprises administering to said host an effective amount of the first polypeptide or second polypeptide of claim 4.

20. A method to vaccinate or treat a mammalian host against dental caries which method comprises administering to said host an effective amount of the first polypeptide or second polypeptide of claim 5.

21. The method of claim 16 wherein said polypeptide or polypeptide is administered by topical application in the mouth.

22. The method of claim 17 wherein said polypeptide or polypeptide is administered by topical application in the mouth.

23. The method of claim 18 wherein said polypeptide or polypeptide is administered by topical application in the mouth.

24. The method of claim 19 wherein said polypeptide or polypeptide is administered by topical application in the mouth.

25. The method of claim 20 wherein said first polypeptide or second polypeptide is administered by topical application in the mouth.

* * * * *

SEQUENCE LISTING

<160> NUMBER OF SEQ ID NOS: 29

<210> SEQ ID NO 1
<211> LENGTH: 190
<212> TYPE: PRT
<213> ORGANISM: Streptococcus mutans

<400> SEQUENCE: 1

Thr Glu Lys Pro Leu Glu Pro Ala Pro Val Glu Pro Ser Tyr Glu Ala
1               5                   10                  15

Glu Pro Thr Pro Pro Thr Pro Thr Pro Asp Gln Pro Glu Pro Asn Lys
                20                  25                  30

Pro Val Glu Pro Thr Tyr Glu Val Ile Pro Thr Pro Pro Thr Asp Pro
            35                  40                  45

```
Val Tyr Gln Asp Leu Pro Thr Pro Pro Ser Ile Pro Thr Val His Phe
    50                  55                  60
His Tyr Phe Lys Leu Ala Val Gln Pro Gln Val Asn Lys Glu Ile Arg
65                  70                  75                  80
Asn Asn Asn Asp Val Asn Ile Asp Arg Thr Leu Val Ala Lys Gln Ser
                85                  90                  95
Val Val Lys Phe Gln Leu Lys Thr Ala Asp Leu Pro Ala Gly Arg Asp
            100                 105                 110
Glu Thr Thr Ser Phe Val Leu Val Asp Pro Leu Pro Ser Gly Tyr Gln
        115                 120                 125
Phe Asn Pro Glu Ala Thr Lys Ala Ala Ser Pro Gly Phe Asp Val Ala
    130                 135                 140
Tyr Asp Asn Ala Thr Asn Thr Val Thr Phe Lys Ala Thr Ala Ala Thr
145                 150                 155                 160
Leu Ala Thr Phe Asn Ala Asp Leu Thr Lys Ser Val Ala Thr Ile Tyr
                165                 170                 175
Pro Thr Val Val Gly Gln Val Leu Asn Asp Gly Ala Thr Tyr
            180                 185                 190

<210> SEQ ID NO 2
<211> LENGTH: 40
<212> TYPE: PRT
<213> ORGANISM: Streptococcus mutans

<400> SEQUENCE: 2

Asn Asn Asn Asp Val Asn Ile Asp Arg Thr Leu Val Ala Lys Gln Ser
1               5                   10                  15
Val Val Lys Phe Gln Leu Lys Thr Ala Asp Leu Pro Ala Gly Arg Asp
            20                  25                  30
Glu Thr Thr Ser Phe Val Leu Val
        35                  40

<210> SEQ ID NO 3
<211> LENGTH: 20
<212> TYPE: PRT
<213> ORGANISM: Streptococcus mutans

<400> SEQUENCE: 3

Leu Ala Thr Phe Asn Ala Asp Leu Thr Lys Ser Val Ala Thr Ile Tyr
1               5                   10                  15
Pro Thr Val Val
            20

<210> SEQ ID NO 4
<211> LENGTH: 110
<212> TYPE: PRT
<213> ORGANISM: Streptococcus mutans

<400> SEQUENCE: 4

Asn Asn Asn Asp Val Asn Ile Asp Arg Thr Leu Val Ala Lys Gln Ser
1               5                   10                  15
Val Val Lys Phe Gln Leu Lys Thr Ala Asp Leu Pro Ala Gly Arg Asp
            20                  25                  30
Glu Thr Thr Ser Phe Val Leu Val Asp Pro Leu Pro Ser Gly Tyr Gln
        35                  40                  45
Phe Asn Pro Glu Ala Thr Lys Ala Ala Ser Pro Gly Phe Asp Val Ala
    50                  55                  60
```

-continued

```
Tyr Asp Asn Ala Thr Asn Thr Val Thr Phe Lys Ala Thr Ala Ala Thr
 65                  70                  75                  80

Leu Ala Thr Phe Asn Ala Asp Leu Thr Lys Ser Val Ala Thr Ile Tyr
                 85                  90                  95

Pro Thr Val Val Gly Gln Val Leu Asn Asp Gly Ala Thr Tyr
            100                 105                 110
```

<210> SEQ ID NO 5
<211> LENGTH: 80
<212> TYPE: PRT
<213> ORGANISM: Streptococcus mutans

<400> SEQUENCE: 5

```
Thr Glu Lys Pro Leu Glu Pro Ala Pro Val Glu Pro Ser Tyr Glu Ala
  1               5                  10                  15

Glu Pro Thr Pro Pro Thr Pro Thr Pro Asp Gln Pro Glu Pro Asn Lys
                 20                  25                  30

Pro Val Glu Pro Thr Tyr Glu Val Ile Pro Thr Pro Thr Asp Pro
             35                  40                  45

Val Tyr Gln Asp Leu Pro Thr Pro Pro Ser Ile Pro Thr Val His Phe
 50                  55                  60

His Tyr Phe Lys Leu Ala Val Gln Pro Gln Val Asn Lys Glu Ile Arg
 65                  70                  75                  80
```

<210> SEQ ID NO 6
<211> LENGTH: 130
<212> TYPE: PRT
<213> ORGANISM: Streptococcus mutans

<400> SEQUENCE: 6

```
Thr Glu Lys Pro Leu Glu Pro Ala Pro Val Glu Pro Ser Tyr Glu Ala
  1               5                  10                  15

Glu Pro Thr Pro Pro Thr Pro Thr Pro Asp Gln Pro Glu Pro Asn Lys
                 20                  25                  30

Pro Val Glu Pro Thr Tyr Glu Val Ile Pro Thr Pro Thr Asp Pro
             35                  40                  45

Val Tyr Gln Asp Leu Pro Thr Pro Pro Ser Ile Pro Thr Val His Phe
 50                  55                  60

His Tyr Phe Lys Leu Ala Val Gln Pro Gln Val Asn Lys Glu Ile Arg
 65                  70                  75                  80

Asn Asn Asn Asp Val Asn Ile Asp Arg Thr Leu Val Ala Lys Gln Ser
                 85                  90                  95

Val Val Lys Phe Gln Leu Lys Thr Ala Asp Leu Pro Ala Gly Arg Asp
            100                 105                 110

Glu Thr Thr Ser Phe Val Leu Val Asp Pro Leu Pro Ser Gly Tyr Gln
            115                 120                 125

Phe Asn
    130
```

<210> SEQ ID NO 7
<211> LENGTH: 52
<212> TYPE: PRT
<213> ORGANISM: Streptococcus mutans

<400> SEQUENCE: 7

```
Glu Thr Gly Lys Lys Pro Asn Ile Trp Tyr Ser Leu Asn Gly Lys Ile
  1               5                  10                  15

Arg Ala Val Asn Leu Pro Lys Val Thr Lys Glu Lys Pro Thr Pro Pro
```

-continued

```
                20                  25                  30
Val Lys Pro Thr Ala Pro Thr Lys Pro Thr Tyr Glu Thr Glu Lys Pro
            35                  40                  45

Leu Lys Pro Ala
        50

<210> SEQ ID NO 8
<211> LENGTH: 70
<212> TYPE: PRT
<213> ORGANISM: Streptococcus mutans

<400> SEQUENCE: 8

Gln Asp Leu Pro Thr Pro Pro Ser Ile Pro Thr Val His Phe His Tyr
  1               5                  10                  15

Phe Lys Leu Ala Val Gln Pro Gln Val Asn Lys Glu Ile Arg Asn Asn
             20                  25                  30

Asn Asp Val Asn Ile Asp Arg Thr Leu Val Ala Lys Gln Ser Val Val
             35                  40                  45

Lys Phe Gln Leu Lys Thr Ala Asp Leu Pro Ala Gly Arg Asp Glu Thr
         50                  55                  60

Thr Ser Phe Val Leu Val
 65                  70

<210> SEQ ID NO 9
<211> LENGTH: 21
<212> TYPE: PRT
<213> ORGANISM: Streptococcus mutans

<400> SEQUENCE: 9

Phe Gln Leu Lys Thr Ala Asp Leu Pro Ala Gly Arg Asp Glu Thr Thr
  1               5                  10                  15

Ser Phe Val Leu Val
             20

<210> SEQ ID NO 10
<211> LENGTH: 312
<212> TYPE: PRT
<213> ORGANISM: Streptococcus mutans

<400> SEQUENCE: 10

Glu Thr Gly Lys Lys Pro Asn Ile Trp Tyr Ser Leu Asn Gly Lys Ile
  1               5                  10                  15

Arg Ala Val Asn Leu Pro Lys Val Thr Lys Glu Lys Pro Thr Pro Pro
             20                  25                  30

Val Lys Pro Thr Ala Pro Thr Lys Pro Thr Tyr Glu Thr Glu Lys Pro
             35                  40                  45

Leu Lys Pro Ala Pro Val Ala Pro Asn Tyr Glu Lys Glu Pro Thr Pro
         50                  55                  60

Pro Thr Arg Thr Pro Asp Gln Ala Glu Pro Lys Lys Pro Thr Pro Pro
 65                  70                  75                  80

Thr Tyr Glu Thr Glu Lys Pro Leu Glu Pro Ala Pro Val Glu Pro Ser
                 85                  90                  95

Tyr Glu Ala Glu Pro Thr Pro Pro Thr Arg Thr Pro Asp Gln Ala Glu
                100                 105                 110

Pro Asn Lys Pro Thr Pro Pro Thr Tyr Glu Thr Glu Lys Pro Leu Glu
             115                 120                 125

Pro Ala Pro Val Glu Pro Ser Tyr Glu Ala Glu Pro Thr Pro Pro Thr
         130                 135                 140
```

```
Pro Thr Pro Asp Gln Pro Glu Pro Asn Lys Pro Val Glu Pro Thr Tyr
145                 150                 155                 160

Glu Val Ile Pro Thr Pro Pro Thr Asp Pro Val Tyr Gln Asp Leu Pro
            165                 170                 175

Thr Pro Pro Ser Ile Pro Thr Val His Phe His Tyr Phe Lys Leu Ala
            180                 185                 190

Val Gln Pro Gln Val Asn Lys Glu Ile Arg Asn Asn Asn Asp Val Asn
            195                 200                 205

Ile Asp Arg Thr Leu Val Ala Lys Gln Ser Val Val Lys Phe Gln Leu
        210                 215                 220

Lys Thr Ala Asp Leu Pro Ala Gly Arg Asp Glu Thr Thr Ser Phe Val
225                 230                 235                 240

Leu Val Asp Pro Leu Pro Ser Gly Tyr Gln Phe Asn Pro Glu Ala Thr
                245                 250                 255

Lys Ala Ala Ser Pro Gly Phe Asp Val Ala Tyr Asp Asn Ala Thr Asn
                260                 265                 270

Thr Val Thr Phe Lys Ala Thr Ala Ala Thr Leu Ala Thr Phe Asn Ala
            275                 280                 285

Asp Leu Thr Lys Ser Val Ala Thr Ile Tyr Pro Thr Val Val Gly Gln
        290                 295                 300

Val Leu Asn Asp Gly Ala Thr Tyr
305                 310
```

<210> SEQ ID NO 11
<211> LENGTH: 30
<212> TYPE: PRT
<213> ORGANISM: Streptococcus mutans

<400> SEQUENCE: 11

```
Gln Asp Leu Pro Thr Pro Pro Ser Ile Pro Thr Val His Phe His Tyr
1               5                   10                  15

Phe Lys Leu Ala Val Gln Pro Gln Val Asn Lys Glu Ile Arg
            20                  25                  30
```

<210> SEQ ID NO 12
<211> LENGTH: 570
<212> TYPE: DNA
<213> ORGANISM: Streptococcus mutans

<400> SEQUENCE: 12

```
acagaaaagc cgttggagcc agcacctgtt gagccaagct atgaagcaga gccaacgcca      60
ccgacaccaa caccagatca accagaacca aacaaacctg ttgagccaac ttatgaggtt     120
attccaacac cgccgactga tcctgtttat caagatcttc caacacctcc atctatacca     180
actgttcatt tccattactt taaactagct gttcagccgc aggttaacaa agaaattaga     240
aacaataacg atgttaatat tgacagaact ttggtggcta acaatctgt tgttaagttc      300
cagctgaaga cagcagatct ccctgctgga cgtgatgaaa caacttcctt tgtcttggta     360
gatcccctgc catctggtta tcaatttaat cctgaagcta caaaagctgc cagccctggc     420
tttgatgtcg cttatgataa tgcaactaat acagtcacct caaggcaac tgcagcaact     480
ttggctacgt ttaatgctga tttgactaag tcagtggcaa cgatttatcc aacagtggtc     540
ggacaagttc ttaatgatgg cgcaacttat                                      570
```

<210> SEQ ID NO 13
<211> LENGTH: 120

```
<212> TYPE: DNA
<213> ORGANISM: Streptococcus mutans

<400> SEQUENCE: 13
aacaataacg atgttaatat tgacagaact ttggtggcta acaatctgt tgttaagttc    60
cagctgaaga cagcagatct ccctgctgga cgtgatgaaa caacttcctt tgtcttggta  120

<210> SEQ ID NO 14
<211> LENGTH: 60
<212> TYPE: DNA
<213> ORGANISM: Streptococcus mutans

<400> SEQUENCE: 14
ttggctacgt ttaatgctga tttgactaag tcagtggcaa cgatttatcc aacagtggtc   60

<210> SEQ ID NO 15
<211> LENGTH: 330
<212> TYPE: DNA
<213> ORGANISM: Streptococcus mutans

<400> SEQUENCE: 15
aacaataacg atgttaatat tgacagaact ttggtggcta acaatctgt tgttaagttc    60
cagctgaaga cagcagatct ccctgctgga cgtgatgaaa caacttcctt tgtcttggta  120
gatcccctgc catctggtta tcaatttaat cctgaagcta caaaagctgc cagccctggc  180
tttgatgtcg cttatgataa tgcaactaat acagtcacct tcaaggcaac tgcagcaact  240
ttggctacgt ttaatgctga tttgactaag tcagtggcaa cgatttatcc aacagtggtc  300
ggacaagttc ttaatgatgg cgcaacttat                                   330

<210> SEQ ID NO 16
<211> LENGTH: 240
<212> TYPE: DNA
<213> ORGANISM: Streptococcus mutans

<400> SEQUENCE: 16
acagaaaagc cgttggagcc agcacctgtt gagccaagct atgaagcaga gccaacgcca    60
ccgacaccaa caccagatca accagaacca aacaaacctg ttgagccaac ttatgaggtt  120
attccaacac cgccgactga tcctgtttat caagatcttc aacacctcc atctatacca   180
actgttcatt tccattactt taaactagct gttcagccgc aggttaacaa agaaattaga  240

<210> SEQ ID NO 17
<211> LENGTH: 390
<212> TYPE: DNA
<213> ORGANISM: Streptococcus mutans

<400> SEQUENCE: 17
acagaaaagc cgttggagcc agcacctgtt gagccaagct atgaagcaga gccaacgcca    60
ccgacaccaa caccagatca accagaacca aacaaacctg ttgagccaac ttatgaggtt  120
attccaacac cgccgactga tcctgtttat caagatcttc aacacctcc atctatacca   180
actgttcatt tccattactt taaactagct gttcagccgc aggttaacaa agaaattaga  240
aacaataacg atgttaatat tgacagaact ttggtggcta acaatctgt tgttaagttc   300
cagctgaaga cagcagatct ccctgctgga cgtgatgaaa caacttcctt tgtcttggta  360
gatcccctgc catctggtta tcaatttaat                                   390

<210> SEQ ID NO 18
```

<211> LENGTH: 156
<212> TYPE: DNA
<213> ORGANISM: Streptococcus mutans

<400> SEQUENCE: 18

```
gaaaccggca aaaaccaaa tatttggtat tcattaaatg gtaaaatccg tgcggttaat    60
cttcctaaag ttactaagga aaaacccaca cctccggtta aaccaacagc tccaactaaa   120
ccaacttatg aaacagaaaa gccattaaaa ccggca                            156
```

<210> SEQ ID NO 19
<211> LENGTH: 210
<212> TYPE: DNA
<213> ORGANISM: Streptococcus mutans

<400> SEQUENCE: 19

```
caagatcttc caacacctcc atctatacca actgttcatt tccattactt taaactagct    60
gttcagccgc aggttaacaa agaaattaga acaataacg atgttaatat tgacagaact   120
ttggtggcta acaatctgt tgttaagttc cagctgaaga cagcagatct ccctgctgga   180
cgtgatgaaa caacttcctt tgtcttggta                                    210
```

<210> SEQ ID NO 20
<211> LENGTH: 63
<212> TYPE: DNA
<213> ORGANISM: Streptococcus mutans

<400> SEQUENCE: 20

```
ttccagctga agacagcaga tctccctgct ggacgtgatg aaacaacttc ctttgtcttg    60
gta                                                                  63
```

<210> SEQ ID NO 21
<211> LENGTH: 936
<212> TYPE: DNA
<213> ORGANISM: Streptococcus mutans

<400> SEQUENCE: 21

```
gaaaccggca aaaaccaaa tatttggtat tcattaaatg gtaaaatccg tgcggttaat    60
cttcctaaag ttactaagga aaaacccaca cctccggtta aaccaacagc tccaactaaa   120
ccaacttatg aaacagaaaa gccattaaaa ccggcaccag tagctccaaa ttatgaaaag   180
gagccaacac caccgacaag aacaccggat caagcagagc caagaaaacc cactccgccg   240
acctatgaaa cagaaaagcc gttggagcca gcacctgttg agccaagcta tgaagcagag   300
ccaacaccgc cgacaaggac accggatcag gcagagccaa ataaacccac accgccgacc   360
tatgaaacag aaaagccgtt ggagccagca cctgttgagc caagctatga agcagagcca   420
acgccaccga caccaacacc agatcaacca gaaccaaaca aacctgttga gccaacttat   480
gaggttattc aacaccgcc gactgatcct gtttatcaag atcttccaac acctccatct   540
ataccaactg ttcatttcca ttactttaaa ctagctgttc agccgcaggt taacaaagaa   600
attagaaaca ataacgatgt taatattgac agaactttgg tgctaaaca atctgttgtt   660
aagttccagc tgaagacagc agatctccct gctggacgtg atgaaacaac ttcctttgtc   720
ttggtagatc ccctgccatc tggttatcaa tttaatcctg aagctacaaa agctgccagc   780
cctggctttg atgtcgctta tgataatgca actaatacag tcaccttcaa ggcaactgca   840
gcaactttgg ctacgtttaa tgctgatttg actaagtcag tggcaacgat ttatccaaca   900
gtggtcggac aagttcttaa tgatggcgca acttat                            936
```

<210> SEQ ID NO 22
<211> LENGTH: 90
<212> TYPE: DNA
<213> ORGANISM: Streptococcus mutans

<400> SEQUENCE: 22

```
caagatcttc caacacctcc atctatacca actgttcatt tccattactt taaactagct    60
gttcagccgc aggttaacaa agaaattaga                                     90
```

<210> SEQ ID NO 23
<211> LENGTH: 1561
<212> TYPE: PRT
<213> ORGANISM: Streptococcus mutans

<400> SEQUENCE: 23

```
Met Lys Val Lys Lys Thr Tyr Gly Phe Arg Lys Ser Lys Ile Ser Lys
 1               5                  10                  15

Thr Leu Cys Gly Ala Val Leu Gly Thr Val Ala Ala Val Ser Val Ala
             20                  25                  30

Gly Gln Lys Val Phe Ala Asp Glu Thr Thr Thr Ser Asp Val Asp
         35                  40                  45

Thr Lys Val Val Gly Thr Gln Thr Gly Asn Pro Ala Thr Asn Leu Pro
     50                  55                  60

Glu Ala Gln Gly Ser Ala Ser Lys Gln Ala Glu Gln Ser Gln Thr Lys
 65                  70                  75                  80

Leu Glu Arg Gln Met Val His Thr Ile Glu Val Pro Lys Thr Asp Leu
                 85                  90                  95

Asp Gln Ala Ala Lys Asp Ala Lys Ser Ala Gly Val Asn Val Val Gln
            100                 105                 110

Asp Ala Asp Val Asn Lys Gly Thr Val Lys Thr Ala Glu Glu Ala Val
        115                 120                 125

Gln Lys Glu Thr Glu Ile Lys Glu Asp Tyr Thr Lys Gln Ala Glu Asp
    130                 135                 140

Ile Lys Lys Thr Thr Asp Gln Tyr Lys Ser Asp Val Ala Ala His Glu
145                 150                 155                 160

Ala Glu Val Ala Lys Ile Lys Ala Lys Asn Gln Ala Thr Lys Glu Gln
                165                 170                 175

Tyr Gly Lys Asp Met Val Ala His Lys Ala Glu Val Glu Arg Ile Asn
            180                 185                 190

Ala Ala Asn Ala Ala Ser Lys Thr Ala Tyr Glu Ala Lys Leu Ala Gln
        195                 200                 205

Tyr Gln Ala Asp Leu Ala Ala Val Gln Lys Thr Asn Ala Ala Asn Gln
    210                 215                 220

Ala Ser Tyr Gln Lys Ala Leu Ala Ala Tyr Gln Ala Glu Leu Lys Arg
225                 230                 235                 240

Val Gln Glu Ala Asn Ala Ala Lys Ala Ala Tyr Asp Thr Ala Val
                245                 250                 255

Ala Ala Asn Asn Ala Lys Asn Thr Glu Ile Ala Ala Asn Glu Glu
            260                 265                 270

Ile Arg Lys Arg Asn Ala Thr Lys Ala Glu Tyr Glu Thr Lys Leu
        275                 280                 285

Ala Gln Tyr Gln Ala Glu Leu Lys Arg Val Gln Glu Ala Asn Ala Ala
    290                 295                 300

Asn Glu Ala Asp Tyr Gln Ala Lys Leu Thr Ala Tyr Gln Thr Glu Leu
```

-continued

```
305                 310                 315                 320
Ala Arg Val Gln Lys Ala Asn Ala Asp Ala Lys Ala Tyr Glu Ala
                325                 330                 335
Ala Val Ala Ala Asn Asn Ala Lys Asn Ala Ala Leu Thr Ala Glu Asn
            340                 345                 350
Thr Ala Ile Lys Gln Arg Asn Glu Asn Ala Lys Ala Thr Tyr Glu Ala
                355                 360                 365
Ala Leu Lys Gln Tyr Glu Ala Asp Leu Ala Ala Val Lys Lys Ala Asn
        370                 375                 380
Ala Ala Asn Glu Ala Asp Tyr Gln Ala Lys Leu Thr Ala Tyr Gln Thr
385                 390                 395                 400
Glu Leu Ala Arg Val Gln Lys Ala Asn Ala Asp Ala Lys Ala Ala Tyr
                405                 410                 415
Glu Ala Ala Val Ala Ala Asn Asn Ala Ala Asn Ala Ala Leu Thr Ala
            420                 425                 430
Glu Asn Thr Ala Ile Lys Lys Arg Asn Ala Asp Ala Lys Ala Asp Tyr
        435                 440                 445
Glu Ala Lys Leu Ala Lys Tyr Gln Ala Asp Leu Ala Lys Tyr Gln Lys
    450                 455                 460
Asp Leu Ala Asp Tyr Pro Val Lys Leu Lys Ala Tyr Glu Asp Glu Gln
465                 470                 475                 480
Ala Ser Ile Lys Ala Ala Leu Ala Glu Leu Glu Lys His Lys Asn Glu
                485                 490                 495
Asp Gly Asn Leu Thr Glu Pro Ser Ala Gln Asn Leu Val Tyr Asp Leu
            500                 505                 510
Glu Pro Asn Ala Asn Leu Ser Leu Thr Thr Asp Gly Lys Phe Leu Lys
        515                 520                 525
Ala Ser Ala Val Asp Asp Ala Phe Ser Lys Ser Thr Ser Lys Ala Lys
    530                 535                 540
Tyr Asp Gln Lys Ile Leu Gln Leu Asp Asp Leu Asp Ile Thr Asn Leu
545                 550                 555                 560
Glu Gln Ser Asn Asp Val Ala Ser Ser Met Glu Leu Tyr Gly Asn Phe
                565                 570                 575
Gly Asp Lys Ala Gly Trp Ser Thr Thr Val Ser Asn Asn Ser Gln Val
            580                 585                 590
Lys Trp Gly Ser Val Leu Leu Glu Arg Gly Gln Ser Ala Thr Ala Thr
        595                 600                 605
Tyr Thr Asn Leu Gln Asn Ser Tyr Tyr Asn Gly Lys Lys Ile Ser Lys
    610                 615                 620
Ile Val Tyr Lys Tyr Thr Val Asp Pro Lys Ser Lys Phe Gln Gly Gln
625                 630                 635                 640
Lys Val Trp Leu Gly Ile Phe Thr Asp Pro Thr Leu Gly Val Phe Ala
                645                 650                 655
Ser Ala Tyr Thr Gly Gln Val Glu Lys Asn Thr Ser Ile Phe Ile Lys
            660                 665                 670
Asn Glu Phe Thr Phe Tyr Asp Glu Asp Gly Lys Pro Ile Asn Phe Asp
        675                 680                 685
Asn Ala Leu Leu Ser Val Ala Ser Leu Asn Arg Glu Asn Asn Ser Ile
    690                 695                 700
Glu Met Ala Lys Asp Tyr Thr Gly Lys Phe Val Lys Ile Ser Gly Ser
705                 710                 715                 720
Ser Ile Gly Glu Lys Asn Gly Met Ile Tyr Ala Thr Asp Thr Leu Asn
                725                 730                 735
```

-continued

```
Phe Arg Gln Gly Gln Gly Ala Arg Trp Thr Met Tyr Thr Arg Ala
            740                 745                 750
Ser Glu Pro Gly Ser Gly Trp Asp Ser Ser Asp Ala Pro Asn Ser Trp
            755                 760                 765
Tyr Gly Ala Gly Ala Ile Arg Met Ser Gly Pro Asn Asn Ser Val Thr
            770                 775                 780
Leu Gly Ala Ile Ser Ser Thr Leu Val Val Pro Ala Asp Pro Thr Met
785                 790                 795                 800
Ala Ile Glu Thr Gly Lys Lys Pro Asn Ile Trp Tyr Ser Leu Asn Gly
            805                 810                 815
Lys Ile Arg Ala Val Asn Leu Pro Lys Val Thr Lys Glu Lys Pro Thr
            820                 825                 830
Pro Pro Val Lys Pro Thr Ala Pro Thr Lys Pro Thr Tyr Glu Thr Glu
            835                 840                 845
Lys Pro Leu Lys Pro Ala Pro Val Ala Pro Asn Tyr Glu Lys Glu Pro
            850                 855                 860
Thr Pro Pro Thr Arg Thr Pro Asp Gln Ala Glu Pro Lys Lys Pro Thr
865                 870                 875                 880
Pro Pro Thr Tyr Glu Thr Glu Lys Pro Leu Glu Pro Ala Pro Val Glu
            885                 890                 895
Pro Ser Tyr Glu Ala Glu Pro Thr Pro Pro Thr Arg Thr Pro Asp Gln
            900                 905                 910
Ala Glu Pro Asn Lys Pro Thr Pro Pro Thr Tyr Glu Thr Glu Lys Pro
            915                 920                 925
Leu Glu Pro Ala Pro Val Glu Pro Ser Tyr Glu Ala Glu Pro Thr Pro
            930                 935                 940
Pro Thr Pro Thr Pro Asp Gln Pro Glu Pro Asn Lys Pro Val Glu Pro
945                 950                 955                 960
Thr Tyr Glu Val Ile Pro Thr Pro Pro Thr Asp Pro Val Tyr Gln Asp
                965                 970                 975
Leu Pro Thr Pro Pro Ser Ile Pro Thr Val His Phe His Tyr Phe Lys
            980                 985                 990
Leu Ala Val Gln Pro Gln Val Asn Lys Glu Ile Arg Asn Asn Asn Asp
            995                 1000                1005
Val Asn Ile Asp Arg Thr Leu Val Ala Lys Gln Ser Val Val Lys Phe
            1010                1015                1020
Gln Leu Lys Thr Ala Asp Leu Pro Ala Gly Arg Asp Glu Thr Thr Ser
1025                1030                1035                1040
Phe Val Leu Val Asp Pro Leu Pro Ser Gly Tyr Gln Phe Asn Pro Glu
            1045                1050                1055
Ala Thr Lys Ala Ala Ser Pro Gly Phe Asp Val Ala Tyr Asp Asn Ala
            1060                1065                1070
Thr Asn Thr Val Thr Phe Lys Ala Thr Ala Thr Leu Ala Thr Phe
            1075                1080                1085
Asn Ala Asp Leu Thr Lys Ser Val Ala Thr Ile Tyr Pro Thr Val Val
            1090                1095                1100
Gly Gln Val Leu Asn Asp Gly Ala Thr Tyr Lys Asn Asn Phe Ser Leu
1105                1110                1115                1120
Thr Val Asn Asp Ala Tyr Gly Ile Lys Ser Asn Val Val Arg Val Thr
            1125                1130                1135
Thr Pro Gly Lys Pro Asn Asp Pro Asp Asn Pro Asn Asn Tyr Ile
            1140                1145                1150
```

-continued

```
Lys Pro Thr Lys Val Asn Lys Asn Glu Asn Gly Val Val Ile Asp Gly
        1155                1160                1165
Lys Thr Val Leu Ala Gly Ser Thr Asn Tyr Tyr Glu Leu Thr Trp Asp
    1170                1175                1180
Leu Asp Gln Tyr Lys Asn Asp Arg Ser Ser Ala Asp Thr Ile Gln Gln
1185                1190                1195                1200
Gly Phe Tyr Tyr Val Asp Asp Tyr Pro Glu Gly Ala Leu Glu Leu Arg
            1205                1210                1215
Gln Asp Leu Val Lys Ile Thr Asp Ala Asn Gly Asn Glu Val Thr Gly
        1220                1225                1230
Val Ser Val Asp Asn Tyr Thr Ser Leu Glu Ala Ala Pro Gln Glu Ile
            1235                1240                1245
Arg Asp Val Leu Ser Lys Ala Gly Ile Arg Pro Lys Gly Ala Phe Gln
        1250                1255                1260
Ile Phe Arg Ala Asp Asn Pro Arg Glu Phe Tyr Asp Thr Tyr Val Lys
1265                1270                1275                1280
Thr Gly Ile Asp Leu Lys Ile Val Ser Pro Met Val Val Lys Lys Gln
            1285                1290                1295
Met Gly Gln Thr Gly Gly Ser Tyr Glu Asp Gln Ala Tyr Gln Ile Asp
        1300                1305                1310
Phe Gly Asn Gly Tyr Ala Ser Asn Ile Val Ile Asn Asn Val Pro Lys
        1315                1320                1325
Ile Asn Pro Lys Lys Asp Val Thr Leu Thr Leu Asp Pro Ala Asp Thr
    1330                1335                1340
Asn Asn Val Asp Gly Gln Thr Ile Pro Leu Asn Thr Val Phe Asn Tyr
1345                1350                1355                1360
Arg Leu Ile Gly Gly Ile Ile Pro Ala Asn His Ser Glu Glu Leu Phe
            1365                1370                1375
Glu Tyr Asn Phe Tyr Asp Asp Tyr Asp Gln Thr Gly Asp His Tyr Thr
            1380                1385                1390
Gly Gln Tyr Lys Val Phe Ala Lys Val Asp Ile Thr Leu Lys Asn Gly
        1395                1400                1405
Val Ile Ile Lys Ser Gly Thr Glu Leu Thr Gln Tyr Thr Thr Ala Glu
    1410                1415                1420
Val Asp Thr Thr Lys Gly Ala Ile Thr Ile Lys Phe Lys Glu Ala Phe
1425                1430                1435                1440
Leu Arg Ser Val Ser Ile Asp Ser Ala Phe Gln Ala Glu Ser Tyr Ile
            1445                1450                1455
Gln Met Lys Arg Ile Ala Val Gly Thr Phe Glu Asn Thr Tyr Ile Asn
            1460                1465                1470
Thr Val Asn Gly Val Thr Tyr Ser Ser Asn Thr Val Lys Thr Thr Thr
        1475                1480                1485
Pro Glu Asp Pro Ala Asp Pro Thr Asp Pro Gln Asp Pro Ser Ser Pro
        1490                1495                1500
Arg Thr Ser Thr Val Ile Ile Tyr Lys Pro Gln Ser Thr Ala Tyr Gln
1505                1510                1515                1520
Pro Ser Ser Val Gln Lys Thr Leu Pro Asn Thr Gly Val Thr Asn Asn
            1525                1530                1535
Ala Tyr Met Pro Leu Leu Gly Ile Ile Gly Leu Val Thr Ser Phe Ser
        1540                1545                1550
Leu Leu Gly Leu Lys Ala Lys Lys Asp
        1555                1560
```

<210> SEQ ID NO 24
<211> LENGTH: 4865
<212> TYPE: DNA
<213> ORGANISM: Streptococcus mutans

<400> SEQUENCE: 24

| | | | | | |
|---|---|---|---|---|---|
| atttcagcaa | aaattgacaa | atcaaatcaa | ttatattaca | attttttaac | gtatattaca | 60 |
| aaatatatt | tggaagattt | attcagattt | ggaggattta | tgaaagtcaa | aaaaacttac | 120 |
| ggttttcgta | aaagtaaaat | tagtaaaaca | ctgtgtggtg | ctgttctagg | aacagtagca | 180 |
| gcagtctctg | tagcaggaca | aaaggttttt | gccgatgaaa | cgaccactac | tagtgatgta | 240 |
| gatactaaag | tagttggaac | acaaactgga | atccagcga | ccatttgcc | agaggctcaa | 300 |
| ggaagtgcga | gtaagcaagc | tgaacaaagt | caaaccaagc | tggagagaca | aatggttcat | 360 |
| accattgaag | tacctaaaac | tgatcttgat | caagcagcaa | agatgctaa | gtctgctggt | 420 |
| gtcaatgttg | tccaagatgc | cgatgttaat | aaggaactg | ttaaaacagc | tgaagaagca | 480 |
| gtccaaaaag | aaactgaaat | taagaagat | tacacaaaac | aagctgagga | tattaagaag | 540 |
| acaacagatc | aatataaatc | ggatgtagct | gctcatgagg | cagaagttgc | taaaatcaaa | 600 |
| gctaaaaatc | aggcaactaa | agaacagtat | ggaaagata | tggtagctca | taaagccgag | 660 |
| gttgaacgca | ttaatgctgc | aaatgctgcc | agtaaaaca | cttatgaagc | taaattggct | 720 |
| caatatcaag | cagatttagc | agccgttcaa | aaaaccaatg | ctgccaatca | agcatcctat | 780 |
| caaaaagccc | ttgctgctta | tcaggctgaa | ctgaaacgtg | ttcaggaagc | taatgcagcc | 840 |
| gccaaagccg | cttatgatac | tgctgtagca | gcaaataatg | ccaaaaatac | agaaattgcc | 900 |
| gctgccaatg | aagaaattag | aaaacgcaat | gcaacggcca | agctgaata | tgagactaag | 960 |
| ttagctcaat | atcaagctga | actaaagcgt | gttcaggaag | ctaatgccgc | aaacgaagca | 1020 |
| gactatcaag | ctaaattgac | cgcctatcaa | acagagcttg | ctcgcgttca | gaaagccaat | 1080 |
| gcagatgcta | agcggccta | tgaagcagct | gtagcagcaa | ataatgccaa | aaatgcggca | 1140 |
| cttacagctg | aaaatactgc | aattaagcaa | cgcaatgaga | atgctaaggc | gacttatgaa | 1200 |
| gctgcactca | agcaatatga | ggctgatttg | gcagcggtga | aaaaagctaa | tgccgcaaac | 1260 |
| gaagcagact | atcaagctaa | attgaccgcc | tatcaaacag | agctcgctcg | cgttcaaaag | 1320 |
| gccaatgcgg | atgctaaagc | ggcctatgaa | gcagctgtag | cagcaaataa | tgccgcaaat | 1380 |
| gcagcgctca | cagctgaaaa | tactgcaatt | aagaagcgca | atgcggatgc | taaagctgat | 1440 |
| tacgaagcaa | aacttgctaa | gtatcaagca | gatcttgcca | aatatcaaaa | agatttagca | 1500 |
| gactatccag | ttaagttaaa | ggcatacgaa | gatgaacaag | cttctattaa | agctgcactg | 1560 |
| gcagaacttg | aaaaacataa | aaatgaagac | ggaaacttaa | cagaaccatc | tgctcaaaat | 1620 |
| ttggtctatg | atcttgagcc | aaatgcgaac | ttatctttga | caacagatgg | gaagttcctt | 1680 |
| aaggcttctg | ctgtggatga | tgcttttagc | aaaagcactt | caaagcaaa | atatgaccaa | 1740 |
| aaaattcttc | aattagatga | tctagatatc | actaacttag | aacaatctaa | tgatgttgct | 1800 |
| tcttctatgg | agctttatgg | caattttggt | gataaagctg | gctggtcaac | gacagtaagc | 1860 |
| aataactcac | aggttaaatg | gggatcggta | cttttagagc | gcggtcaaag | cgcaacagct | 1920 |
| acatacacta | acctgcagaa | ttcttattac | gtccaagttt | caaggtcaaa | aggtttggtt | 1980 |
| aggtattttt | accgatccaa | aatggtaaaa | agatttctaa | aattgtctac | aagtatacag | 2040 |
| tggaccctaa | ctttaggtgt | ttttgcttcc | gcttatacag | gtcaagttga | aaaaacact | 2100 |
| tctattttta | ttaaaaatga | attcactttc | tatgacgaag | atggaaaacc | aattaatttt | 2160 |

-continued

```
gataatgccc ttctatcagt agcttctctt aaccgagaaa ataattctat tgagatggcc     2220
aaagattata cgggtaaatt tgtcaaaatc tctggatcat ctatcggtga aaagaatggc     2280
atgatttatg ctacagatac tctcaactt aggcagggtc aaggtggtgc tcgttggacc      2340
atgtatacca gagctagcga accgggatct ggctgggata gttcagatgc gcctaactct     2400
tggtatggtg ctggtgctat ccgcatgtct ggtcctaata acagtgtgac tttgggtgct    2460
atctcatcaa cacttgttgt gcctgctgat cctacaatgg caattgaaac cggcaaaaaa    2520
ccaaatattt ggtattcatt aaatggtaaa atccgtgcgg ttaatcttcc taaagttact    2580
aaggaaaaac ccacacctcc ggttaaacca acagctccaa ctaaaccaac ttatgaaaca    2640
gaaaagccat aaaaccggc accagtagct ccaaattatg aaaaggagcc aacaccaccg     2700
acaagaacac cggatcaagc agagccaaag aaacccactc cgccgaccta tgaaacagaa    2760
aagccgttgg agccagcacc tgttgagcca agctatgaag cagagccaac accgccgaca    2820
aggacaccgg atcaggcaga gccaaataaa cccacaccgc cgacctatga aacagaaaag    2880
ccgttggagc cagcacctgt tgagccaagc tatgaagcag agccaacgcc accgacacca    2940
acaccagatc aaccagaacc aaacaaacct gttgagccaa cttatgaggt tattccaaca    3000
ccgccgactg atcctgttta tcaagatctt ccaacacctc catctatacc aactgttcat    3060
ttccattact ttaaactagc tgttcagccg caggttaaca aagaaattag aaacaataac    3120
gatgttaata ttgacagaac tttggtggct aaacaatctg ttgttaagtt ccagctgaag    3180
acagcagatc tccctgctgg acgtgatgaa acaacttcct ttgtcttggt agatcccctg    3240
ccatctggtt atcaatttaa tcctgaagct acaaaagctg ccagccctgg ctttgatgtc    3300
gcttatgata atgcaactaa tacagtcacc ttcaaggcaa ctgcagcaac tttggctacg    3360
tttaatgctg atttgactaa gtcagtggca acgatttatc caacagtggt cggacaagtt    3420
cttaatgatg gcgcaactta taagaataat ttctcgctca cagtcaatga tgcttatggc    3480
attaaatcca atgttgttcg ggtgacaact cctggtaaac caaatgatcc agataaccca    3540
aataataatt acattaagcc aactaaggtt aataaaaatg aaaatggcgt tgttattgat    3600
ggtaaaacag ttcttgccgg ttcaacgaat tattatgagc taacttggga tttggatcaa    3660
tataaaaacg accgctcttc agcagatacc attcaacaag gattttacta tgtagatgat    3720
tatccagaag aagcgcttga attgcgtcag gatttagtga agattacaga tgctaatggc    3780
aatgaagtta ctggtgttag tgtggataat tatactagtc ttgaagcagc ccctcaagaa    3840
attagagatg ttcttctaa ggcaggaatt agacctaaag gtgctttcca aattttccgt     3900
gccgataatc caagagaatt ttatgatact tatgtcaaaa ctggaattga tttgaagatt    3960
gtatcaccaa tggttgttaa aaaacaaatg ggacaaacag gcgggagtta tgaagatcaa    4020
gcttaccaaa ttgactttgg taatggttat gcatcaaata tcgttatcaa taatgttcct    4080
aagattaacc ctaagaaaga tgtgacctta acacttgatc cggctgatac aaataatgtt    4140
gatggtcaga ctattccact taatacagtc tttaattacc gtttgattgg tggcattatc    4200
cctgcaaatc actcagaaga actctttgaa tacaatttct atgatgatta tgatcaaaca    4260
ggagatcact atactggtca gtataaagtt tttgccaagg ttgatatcac tcttaaaaac    4320
ggtgttatta tcaagtcagg tactgagtta actcagtata cgacagcgga agttgatacc    4380
actaaaggtg ctatcacaat taagttcaag gaagcctttc tgcgttctgt ttcaattgat    4440
tcagccttcc aagctgaaag ttatatccaa atgaaacgta ttgcggttgg tacttttgaa    4500
aatacctata ttaatactgt caatggggta acttacagtt caaatacagt gaaaacaact    4560
```

-continued

```
actcctgagg atcctgcaga ccctactgat ccgcaagatc catcatcacc gcggacttca      4620
actgtaatta tctacaaacc tcaatcaact gcttatcaac caagctctgt ccaaaaaacg      4680
ttaccaaata cgggagtaac aaacaatgct tatatgcctt tacttggtat tattggctta     4740
gttactagtt ttagtttgct tggcttaaag gctaagaaag attgacagca tagatattac     4800
attagaatta aaaagtgaga tgaagcgata aatcacagat tgagcttta tctcattttt     4860 tgatt                                                                  4865

<210> SEQ ID NO 25
<211> LENGTH: 33
<212> TYPE: DNA
<213> ORGANISM: Streptococcus mutans

<400> SEQUENCE: 25
atacatatgc caactgttca tttccattac ttt                                   33

<210> SEQ ID NO 26
<211> LENGTH: 36
<212> TYPE: DNA
<213> ORGANISM: Streptococcus mutans

<400> SEQUENCE: 26
gccattgtcg actcattcat ttttattaac cttagt                                36

<210> SEQ ID NO 27
<211> LENGTH: 20
<212> TYPE: PRT
<213> ORGANISM: Streptococcus mutans

<400> SEQUENCE: 27

His Gln Ala Ala Met Gln Ile Ile Arg Asp Ile Ile Asn Glu Glu Ala
 1               5                  10                  15

Ala Asp Trp Asp
            20

<210> SEQ ID NO 28
<211> LENGTH: 36
<212> TYPE: DNA
<213> ORGANISM: Artificial Sequence
<220> FEATURE:
<223> OTHER INFORMATION: Primer

<400> SEQUENCE: 28
tatcatatgc aagatcttcc aacacctcca tctata                                36

<210> SEQ ID NO 29
<211> LENGTH: 30
<212> TYPE: DNA
<213> ORGANISM: Artificial Sequence
<220> FEATURE:
<223> OTHER INFORMATION: Primer

<400> SEQUENCE: 29
gtcgactcat accaagacaa aggaagttgt                                       30
```